(12) United States Patent
Yannoni et al.

(10) Patent No.: US 7,364,870 B2
(45) Date of Patent: Apr. 29, 2008

(54) MK2 INTERACTING PROTEINS

(75) Inventors: Yvonne M. Yannoni, Weston, MA (US); Lih-Ling Lin, Concord, MA (US)

(73) Assignee: Wyeth, Madison, MI (US)

( * ) Notice: Subject to any disclaimer, the term of this patent is extended or adjusted under 35 U.S.C. 154(b) by 0 days.

(21) Appl. No.: 10/523,014

(22) PCT Filed: Aug. 1, 2003

(86) PCT No.: PCT/US03/23981

§ 371 (c)(1),
(2), (4) Date: Feb. 1, 2005

(87) PCT Pub. No.: WO2004/012660

PCT Pub. Date: Feb. 12, 2004

(65) Prior Publication Data

US 2006/0094101 A1    May 4, 2006

Related U.S. Application Data

(60) Provisional application No. 60/400,044, filed on Aug. 2, 2002.

(51) Int. Cl.
*C12Q 1/48* (2006.01)
*C12N 9/20* (2006.01)
(52) U.S. Cl. .................................. 435/15; 435/194
(58) Field of Classification Search .............. 435/15, 435/194
See application file for complete search history.

(56) References Cited

U.S. PATENT DOCUMENTS

| | | | |
|---|---|---|---|
| 4,522,811 A | 6/1985 | Eppstein et al. | |
| 4,554,101 A | 11/1985 | Hopp | |
| 4,609,546 A | 9/1986 | Hiratani | |
| 4,640,835 A | 2/1987 | Shimizu et al. | |
| 4,766,106 A | 8/1988 | Katre et al. | |
| 4,791,192 A | 12/1988 | Nakagawa et al. | |
| 5,116,944 A | 5/1992 | Sivam et al. | |
| 5,414,135 A | 5/1995 | Snow et al. | |
| 5,864,020 A | 1/1999 | Bennett et al. | |
| 6,420,338 B1 * | 7/2002 | Schneider et al. | 514/12 |

FOREIGN PATENT DOCUMENTS

WO    WO 87/05330    9/1987

OTHER PUBLICATIONS

"Mammalian Matchmaker Two-Hybrid Assay Kit User Manual", Clontech, PR17119 (2001).
Altschul et al., "Basic Local Alignment Search Tool," J. Mol. Biol., 215(3):403-10 (1990).
Aplin and Wriston, "Preparation, Properties, and Applications of Carbohydrate Conjugates of Proteins and Lipids," CRC Crit. Rev. Biochem., 22:259-306 (1991).
Bhadra et al., "Pegnology: a review of PEG-ylated systems," Pharmazie, 57:5-29 (2002).
Burke, Protein-Protein Interactions, Pathways and Screens, 21-24 (Mar. 2003).
Edge et al., "Deglycosylation of Glycoproteins by Trifluoromethanesulfonic Acid," Anal. Biochem., 118(1):131-37 (1981).
Falb et al., "Chemical Genomics: Bridging the Gap Between the Proteome and Therapeutics," Current Opinion In Drug Discovery & Development 5(4):532-39 (2002).
Fields and Song, "A Novel Genetic System to Detect Protein-Protein Interactions," Nature, 340:245-246 (1989).
Fields et al., "The Two-Hybrid System: An Assay for Protein-Protein Interactions," Trends in Genetics, 10:286-292 (1994).
Fraley et al., "New Generation Liposomes: The Engineering of an Efficient Vehicle for Intracellular Delivery of Nucleic Acids," Trends Biochem. Sci., 6:77-80 (1981).
Guidez et al., "Recruitment of the Nuclear Receptor Corepressor N-CoR by the TEL Moiety of the Childhood Leukemia-Associated TEL-AML1 Oncoprotein," Blood, 96 (7):2557-2561 (2000).
Gunster, et al., Identification and Characterization of Interaction between the Vertebrate Polycomb-Group Protein BMI1 and Human Homologs of Polyhomeotic, Molecular and Cellualr Biology, 17:2326-2335 (1997).
Hakimuddin et al., "A Chemical Method of the Deglycosylation of Proteins," Arch. Biochem. Biophys., 259:52 (1987).
Han et al., "Emerging Targets for Anti-Inflammatory Therapy, Nature Cell Biology," 1:E39-40 (1999).
Harris et al., "Pegylation: A Novel Process for Modifying Pharmacokinetics," Clin. Pharmacokinet., 40:539-551 (2001).
Heidenreich, et al., "MAPKAP Kinase 2 Phsophorylates Serum Response Factor In Vitro and in Vivo," J. Biological Chemistry, 274(20):14434-14443 (1999).
Huang et al. "LSP1 is the Major Substrate for Mitogen-activated Protein Kinase-activated Protein Kinase 2 in Human Neutrophils", Journal of Biological Chemistry, 272(1):17-19 (1997).
Huot et al., "Oxidative Stress-Induced Actin Reorganization Mediated by the p38 Mitogen-Activated Protein Kinase/Heat Shock Protein 27 Pathway in Vascular Endothelial Cells," Cir. Res., 80(3):383-92 (1997).
Janknecht, "Cell Type-specific Inhibition of the ETS Transcription Factor ER81 by Mitogen-activated Protein Kinase-activated Protein Kinase 2," J. Biological Chemistry, 276(45):41856-14861 (2001).
Koylyarov et al., "Distinct Cellular Functions of MK2, Molecular and Cellular Biology," 22 (13):4827-4835 (2002).
Kotlyarov et al., "MAPKAP Kinase 2 is Essential for LPS-induced TNF-α Biosynthesis," Nature Cell Biol., 1:94-97 (1997).
Krämer, et al., "A Novel Isoform of the Smooth Muscle Cell Differentiation Marker Smoothelin", J Mol. Med., 77:294-98 (1999).

(Continued)

*Primary Examiner*—Maryam Monshipouri
(74) *Attorney, Agent, or Firm*—Finnegan, Henderson, Farabow, Garret & Dunner, LLP

(57) ABSTRACT

The present invention relates to uses of proteins that bind MK2 to modulate inflammation. More particularly, the invention relates to uses of proteins that bind MK2 for treating condition that are related to inflammation. The invention is useful for treating inflammatory conditions, particularly those in which a decrease in inflammation would be therapeutically beneficial.

6 Claims, 20 Drawing Sheets

OTHER PUBLICATIONS

Kyte et al., "A Simple Method for Displaying the Hydropathic Character of a Protein," J. Mol. Biol., 157:105-132 (1982).

Lehner et al., "Mitogen-Activated Protein Kinase-Activated Protein Kinase 2-Dificient Mice Show Increased Susceptibility to Listeria *Monocytogenes* Infection", 168(9):4668-4673 (2002).

Lipman et al., "Rapid and Sensitive Protein Similarity Searches;" Science, 227(4693):1435-41 (1985).

Luban, et al., "The Yeast Two-Hybrid System for Studying Protein-Protein Interactions," Curr. Opinion Biotechnology, 6:59-64 (1995).

Luzi et al., "Evolution of Shc Functions from Nematode to Human," Curr. Opin. Genetics and Development, 10:668-674 (2000).

Mahtani et al., "Mitogen-Activated Protein Kinase p38 Controls the Expression and Postranslation Modification of Tristetraprolin, a Regulator of Tumor Necrosis Factor Alpha mRNA Stability," Molecular and Cellular Biology, 21:6461-6469 (2001).

Mannino et al., "Lipsome Mediated Gene Transfer," Biotechniques, 6(7):682-90 (1988).

Migliaccio et al., "The p66$^{shc}$ Adaptor Protein Controls Oxidative Stress Response and Life Span in Mammals," Nature, 402:309-313 (1999).

Neininger et al., "FRET-based Detection of Different Conformations of MK2," EMBO Reports, 2:703-708 (2001).

Neufeld et al., "Serine/Threonine Kinases 3pK and MAPK-activated Protein Kinase 2 Interact with the Basic Helix-Loop-Helix Transcription Factor E47 and Repress Its Transcriptional Activity," J. Biological Chemistry, 275 (27):20239-20242 (2000).

Pearson, et al., "Improved Tools for Biological Sequence Comparison," Proc. Natl. Acad. Sci. USA, 85:2444-2448 (1988).

Rane, et al., "p38 Kinase-dependent MAPKAPK-2 Activation Functions as 3-Phosphoinositide-dependent Kinase-2 Akt in Human Neutrophils," J. Biological Chemistry, 276(5):3517-3523 (2001).

Rouse et al., "A Novel Kinase Cascade Triggered by Stress and Heat Schock that Stimulates MAPKAP Kinase-2 and Phosphorylation of the Small Heat Shock Proteins", Cell, 78:1027-10237 (1994).

She et al., ERKs and p38 Kinase Phosphorylate p53 Protein at Serine 15 in Response to UV Radiation, J. Biological Chemistry, 275,(27):20444-20449 (2000).

She et al., "Role of MAP Kinases in UVB-Induced Phosphorylation of p53 at Serine 20," Oncogene 21(10):1580-9 (2002).

Smith et al., "Overlapping Genes and Information Theory," J. Theor. Biol., 91(2):379-80 (1981).

Sojar et al., "A Chemical Method for the Deglycosylation of Proteins," Arch. of Biochem. and Biophysics, 259 (1):52-57 (1987).

Stokoe et al. "The Substrate Specificity and Structure of Mitogen-Activated Protein (MAP) Kinase-Activated Protein Kinase-2," Biochem. J. 296:843-849 (1993).

Thotakura et al., "Enzymatic Deglycosylatin of Glycoproteins," Meth. Enzymol., 138:350-59 (1987).

Trinei et al., "A p-53-p66Shc Signalling Pathway Controls Intracellular Redox Status, Levels of Oxidation-Damaged DNA and Oxidative Stress-Inducted Apoptosis," Oncogene 21(24):3872-78 (2002).

Van Der Loop, et al., "Smoothelin, a Novel Cytoskeletal Protein Specific for Smooth Muscle Cells," J. Cell Biology, 134 (2):401-411 (1996).

Vidal et al., "Survey and Summary, Yeast Forward and Reverse 'n'-hybrid Systems," Nucleic Acids Research 27(4):919-929 (1999).

International Search Report, Aug. 22, 2005.

Upton, J., "California's non-profit community blood bank system," California Medical Association, 73: 1950-52 (1950).

Plath, K., et al., "Characterization of the proline rich region of MAPKAP kinase 2: influence on catalytic properties and binding to the C-ABL SH3 domain in vitro," Biochemical and Biophysical Research Communications, 203: 1188-94 (1994).

Supplementary partial European Search Report, mailed May 23, 2007.

Honma, S., et al., "The influence of inflammatory cytokines on estrogen production and cell proliferation in human breast cancer cells," Endocrine Journal, 49: 371-77 (2002).

Yannoni, Y., et al., "P66$^{sch}$A interacts with MAPKAP kinase 2 and regulates its activity," FEBS Letters, 564: 205-11 (2004).

* cited by examiner cccacgcgtccgggggacggttgctgagcgggcctgggacagcgggtcgcggcacctcccgcctgcgcgtgtctaatc cgtctgtcgggtcccgaaagagctaagccgagcctgcgccggacgggtgggctggactgagagaattctctgagctgg tgacaggtgccacaggcactggggatctcaccagaaaggaaccgacggagctaggggccagcgagatggcggac gaggccttagctgggctggatgagggagcccttcggaagctgctggaggtcacagcagatctggcagagcggcggcg catccgctcagccatccgggaactgcagcggcaggagctggagcgcgaggaggaggccctggcatccaagcgtttc cgtgccgagcggcaggacaacaaggagaactggctgcactctcagcagcgggaagctgagcagcgggctgccctg gcacggctggcagggcagctggagtccatgaacgatgtggaggaattgactgcactgttgcgaagcgctggtgagtat gaggagcgcaagctgatccgagctgccatccgccgtgtacgggctcaggagattgaggctgccaccttggctgggag gttgtacagcgggcgtcccaacagtggctcaagagaggacagcaaggggctagcggcacacaggctggaacagtgt gaggtgccagagcgagaggaacaggaacagcaggcagaggtttcaaagccaaccccacccctgaaggcaccag ccaggatgtgaccacagtgacactcctgctgcgagccccacctgggagcacatccagctcacctgcctcacccagcag ttcacccacccctgcctctcctgagcctccattggagcctgccgaggcccagtgccttacagctgaggttccaggcagcc cagagccaccccccagcccacccaagaccaccagccctgagcctcaggagtctccaacgctccccagcactgaggg ccaggtggtcaacaagcttctgtctggccccaaagagacccctgctgcccagagccccaccagaggcccctctgacac caagagagcagacgtggctggaccccgaccctgccaacgctccctgtcggtgctcagccccgccaaccagcccag aaccgagagtccacccccttgccagcggaccttcctcattccagcgggctggctctgtgcgggatcgtgtccacaagtt cacatctgattctcctatggctgctaggctccaggatggcacaccccaggctgccctaagtcccctgacccccgcaaggc tcctgggcccctccctcaccagcaccacccctgcctcctcctccagcggctcctcctctcggggccccagtgatacctcct cccggttcagcaaggagcaacgaggagtagcccagcccctggcccagcttcgaagctgccccaggaggagggcc ccaggggcgcggggcttggctgctaggccccttgaaaacagagcaggggggcctgtggcacgttcagaggagcctggt gccccgctgcccgtggccgtcggcactgccgagccaggggggcagtatgaagaccacattcaccatcgagatcaagg acggccgtggccaggcctccacaggccgggtgctgctgcccacaggcaaccagagggcagaactgacactggggc tgcgggcgcccccgaccctactcagcaccagtagtgggggcaagagcaccatcacccgtgtcaacagccctgggac cctggctcggctgggcagtgtcactcatgtcaccagcttcagccatgccccccccagtagccgaggaggctgcagcatc aagatggaaccagagccagcagagcctctcgctgcagcagtggaagcggccaatggggctgagcagacccgagtg aacaaagcaccagaagggcggagccctctgagcgctgaggagctgatgactattgaggatgaaggagtcttggaca agatgctggatcagagcacggactttgaagagcggaagctcatccgggctgcacttcgtgagctccgacaaaggaag agagaccagcgggacaaggagcgggaacggcggctgcaggaggcacggggccggccaggggaggggcgcgg

*FIG. 1A* caacacagccactgagaccaccacgaggcacagccagcgggcagctgatggctctgctgtcagcactgttaccaag
actgagcggctcgtccactccaatgatggcacacggacggcccgcaccaccacagtggagtcgagtttcgtgaggcg
ctcggagaatggcagtggcagcaccatgatgcaaaccaagaccttctcctcttcctcctcatccaagaagatgggcagc
atcttcgaccgcgaggaccaggccagcccacgggccggcagcctggcggcgctcgagaaacggcaggccgagaa
gaagaaagagctgatgaaggcgcagagtctgcccaagacctcagcctcccaggcgcgcaaggccatgattgagaa
gctggagaaggagggcgcggccggcagccctggcggaccccgcgcagccgtgcagcgatccaccagcttcggggt
ccccaacgccaacagcatcaagcagatgctgctggactggtgtcgagccaagactcgcggctacgagcacgtcgac
atccagaacttctcctccagctggagtgatgggatggccttctgtgccctggtgcacaacttcttccctgaggccttcgactat
gggcagcttagccctcagaaccgacgccagaacttcgaggtggccttctcatctgcggagacccatgcggactgcccg
cagctcctggatacagaggacatggtgcggcttcgagagcctgactggaagtgcgtgtacacgtacatccaggaattct
accgctgtctggtccagaagggggctggtaaaaaccaaaaagtcctaaccccctgctcggggcccacggatgctggtgg
actgtgtgccctggtggaggtggacgacatgatgatcatgggcaagaagcctgaccccaagtgtgtcttcacctatgtg
cagtcgctctacaaccacctgcgacgccacgaactgcgcctgcgcggcaagaatgtctagcctgcccgcccgcatggc
cagccagtggcaagctgccgcccccactctccgggcaccgtctcctgcctgtgcgtccgcccaccgctgccctgtctgttg
cgacaccctccccccacatacacacgcagcgttttgataaattattggttttcaacgaaaaaaaaaaaaaaa

FIG. 1B ggcgccgcatgtgtctccgcggcggctgcagccctcgagcgcccgccgccgcgccccaaccccggccgccgcccgc
cctcccgccccggcctcgcgccccgtcccggcctcgcgccccggccgcccttgttgacgccggccaggccgtgcggt
cggatgcgccgcggcagccccgggccccggctcggaggctccggggcgagaggaggcggcccgccggccggg
accccgcgcgagtcggccccggccaggggctgcgtaggcccgcccggccaggcccagccgcctggacagagaca
gggcagggcattgttcatgcactgaccgacctcagcatccccggcatgacctcagggaacggaaactctgcctccagc
atcgccggcactgcccccagaatggtgagaataaaccaccacaggccattgtgaaacccaaatcctgacgcatgtt
atcgaagggtttgtgatccaggaggggggcggacgtttcccggtgggacgctcgtctgctggtggggaatctcaagaaga
agtatgcacaggggttcctgcctgagaaacttccacagcaggatcacaccaccaccactgactcggagatggaggag
ccctatctgcaagaatccaaagaggagggtgctcccctcaaactcaagtgtgagctctgtggccgggtggactttgcctat
aagttcaagcgttccaagcgcttctgttccatggcttgtgcaaagaggtacaacgtgggatgcaccaaacgggtgggact
tttccactcagaccggagcaagctgcagaaggcaggagctgcgacccacaaccgccgtcggccagcaaagccagtc
tgccaccacttaccaaggataccaagaagcagccaacaggcactgtgccccttcggttactgctgctttgcgtaacaca
cagccaggaagactccagccgttgctcagataactcaagctatgaggaacccttgtcacccatctcagccagctcatcta
cttccgccggcgacaaggccagcgggacctggagctccccgacatgcatatgcgggacctggtgggcatgggacacc
acttcctgccaagtgagccaccaagtgaatgtagaagacgtctacgaattcatccgctctctgccaggctgccaggagat
agcagaggaattccgtgcccaggaaatcgacgggcaagccctgctgctgctcaaggaggaccacctgatgagcgttat
gaacatcaagctggggcccgccctgaagatctacgcccgcatcagcatgctcaaggactcctagggctggtggcacca
ggattctggcccagggcgcctcctcccgactgagcagagccagacagacattcctgaggggcccagaaatggcggc
gttggagggcaggggctctccctaggggcatagctggtgaggaggtctgggcacctcctccatggctctcaggggccttt
catttctgtgggaggggcagagaggtaggtggcacagaagatggggctttatgcttgtaaatattgatagcactggcttcct
ccaaagtcccaatactctagccccgctctcttcccctctttctgtcccccattttccaggggggtatatggtcagggctccccaa
cctgagttggttacttcaagggcagccagcaggcctggatggaggcctagaaagcccttgccttccttcctcccacttctttc
tccaggcctggttaactcttccgttgtcagcttctcccccttcagcctgtttctgcagcagccagggttctcccccctacaccct
ctgcaggtggagagagagaagctgggcccagccgcggtgcctgctggccaagacgccttaacgctgtgtgtatgactg
tgtgactgtgtgggagcctggactgacagataggccaagggctactctctggcatctccaggtgttttgtagcaaacagcc
acttagtgctttgtcctggactccactcagcctcaggatggggaatagccaagaatggcagcctcagcgcagaggcaag
gtcagaaagagacggcgcttcagagtttcctttccagacacccctcccccgcactgtgaagttcccctgaccg

*FIG. 2A* ccctcctggttcacaaagagcattaagaaagctgcggtggtctgagcaacatagcccagacgtggagcctcctggcctg
cctgcccgcccaccctgggagtccagtggtgaggctcagagaacttctaaggggaaagaacagctggagtttctgttga
tgtgaagaaggcagctcttggcctcccactcccacacttctttgcctataaatcttcctagcagcaatttgagctacctgagg
aggaggcagggcagaagggcaagggcctgcctctgacctgccgtgtcctttgcaggaaggaggtaggcacctttctga
gcttattctattccccacccacacccccaggcagggttggaaatgaaggactttttaacctttgttttgttttttaaaaataaat
ctgtaaaatctgaaaaaaaaaaaaaa

FIG. 2B atggggcctgaaactgtctgggtctgagctggggagcggaagccacttgtccctctccctccccaggacttctgtgactcct
gggccacagaggtccaaccagggtaagggcctggggatacccctgcctggccccttgcccaaactggcaggggg
gccaggctgggcagcagcccctctttcacctcaactatggatctcctgccccccaagcccaagtacaatccactccgga
atgagtctctgtcatcgctggaggaaggggcttctgggtccaccccccggaggagctgccttcccatcagcttcatccc
tggggcccatcctgcctcctctgcctggggacgatagtcccactaccctgtgctccttcttccccggatgagcaacctgag
gctggccaacccggctgggggcgcccagggtctaaggggggagccaggaagggcagctgatgatggggagggga
tcgatggggcagccatgccagagtcaggccccctacccctcctccaggacatgaacaagctgagtggaggcggcgg
gcgcaggactcgggtggaaggggggccagcttggggcgaggagtggacccgccacgggagctttgtcaataagccc
acgcggggctggctgcatcccaacgacaaagtcatgggacccggggtttcctacttggttcggtacatgggttgtgtgga
ggtcctccagtcaatgcgtgccctggacttcaacacccggactcaggtcaccagggaggccatcagtctggtgtgtgag
gctgtgccgggtgctaaggggggcgacaaggaggagaaagccctgtagccgcccgctcagctctatcctggggagga
gtaacctgaaatttgctggaatgccaatcactctcaccgtctccaccagcagcctcaacctcatggccgcagactgcaaa
cagatcatcgccaaccaccacatgcaatctatctcatttgcatccggcggggatccggacacagccgagtatgtcgccta
tgttgccaaagaccctgtgaatcagagagcctgccacattctggagtgtcccgaagggcttgcccaggatgtcatcagca
ccattggccaggccttcgagttgcgcttcaaacaatacctcaggaacccacccaaactggtcaccctcatgacaggat
ggctggctttgatggctcagcatgggatgaggaggaggaagagccacctgaccatcagtactataatgacttcccgggg
aaggaaccccccttggggggggtggtagacatgaggcttcgggaaggagccgctccaggggctgctcgacccactgc
acccaatgcccagaccccagccacttgggagctacattgcctgtaggacagcctgttgggggagatccagaagtccg
caaacagatgccacctccaccaccctgtccaggcagagagcttttgatgatccctcctatgtcaacgtccagaacctag
acaaggcccggcaagcagtgggtggtgctgggccccccaatcctgctatcaatggcagtgcaccccgggacctgtttg
acatgaagcccttcgaagatgctcttcgggtgcctccacctcccagtcggtgtccatggctgagcagctccgaggggag
ccctggttccatgggaagctgagccggcgggaggctgaggcactgctgcagctcaatggggacttcttggtacgggag
agcacgaccacacctggccagtatgtgctcactggcttgcagagtgggcagcctaagcatttgctactggtggaccctga
gggtgtggttcggactaaggatcaccgctttgaaagtgtcagtcaccttatcagctaccacatggacaatcacttgcccatc
atctctgcgggcagcgaactgtgtctacagcaacctgtggagcggaaactgtgatctgccctagcgctctcttccagaag
atgccctccaatcctttccaccctattccctaactctcgggacctcgtttgggagtgttctgtgggcttggccttgtgtcagagct
gggagtagcatggactctgggtttcatatccagctgagtgagagggtttgagtcaaaagcctgggtgagaatcctgcctct
ccccaaacattaatcaccaaagtattaatgtacagagtggcccctcacctgggcctttcctgtgccaacctgatgccctt

*FIG. 3A* ccccaagaaggtgagtgcttgtcatggaaaatgtcctgtggtgacaggcccagtggaacagtcacccttctgggcaagg
gggaacaaatcacacctctgggcttcagggtatcccagacccctctcaacacccgccccccccatgtttaaactttgtgcc
tttgaccatctcttaggtctaatgatatttttatgcaaacagttcttggaccccctgaattcttcaatgacagggatgccaacacct
tcttggcttctgggacctgtgttcttgctgagcaccctctccggtttgggttgggataacagaggcaggagtggcagctgtcc
cctctccctggggatatgcaaccccttagagattgccccagagccccactcccggccaggcgggagatggacccctccct
tgctcagtgcctcctggccggggcccctcaccccaaggggtctgtatatacatttcataaggcctgccctcccatgttgcat
gcctatgtactctgcgccaaagtgcagcccttcctcctgaagcctctgccctgcctcccttctgggagggcggggtgggg
gtgactgaatttgggcctcttgtacagttaactctcccaggtggattttgtggaggtgagaaaaggggcattgagactataa
agcagtagacaatccccacataccatctgtagagttggaactgcattcttttaaagtttatatgcatatattttagggctgcta
gacttacttttcctattttcttttccattgcttattcttgagcacaaaatgataatcaattattacatttatacatcaccttttttgacttttc
caagccccttttacagctcttggcattttcctcgcctaggcctgtgaggtaactgggatcgcacccttttataccagagacctga
ggcagatgaaatttatttccatctaggactagaaaaacttgggtctcttaccgcgagactgagaggcagaagtcagcccg
aatgcctgtcagtttcatggaggggaaacgcaaaacctgcagttcctgagtaccttctacaggcccggcccagcctagg
cccggggtggccacaccacagcaagccggcccccccctcttttggccttgtggataagggagagttgaccgttttcatcctg
gcctccttttgctgtttggatgtttccacgggtctcacttataccaaagggaaaactcttcattaaagtccgtatttcttctaaaa
aaaaaaaaaaaaaatacatttatacatcaccttttttgacttttccaagccccttttacagctcttggcattttcctcgcctaggc
ctgtgaggtaactgggatcgcacccttttataccagagacctgaggcagatgaaatttatttccatctaggactagaaaaac
ttgggtctcttaccgcgagactgagaggcagaagtcagcc

FIG. 3B

MADEALAGLDEGALRKLLEVTADLAERRRIRSAIRELQRQELEREEEALASKRFRAER
QDNKENWLHSQQREAEQRAALARLAGQLESMNDVEELTALLRSAGEYEERKLIRAAI
RRVRAQEIEAATLAGRLYSGRPNSGSREDSKGLAAHRLEQCEVPEREEQEQQAEVS
KPTPTPEGTSQDVTTVTLLLRAPPGSTSSSPASPSSSPTPASPEPPLEPAEAQCLTAE
VPGSPEPPPSPPKTTSPEPQESPTLPSTEGQVVNKLLSGPKETPAAQSPTRGPSDTK
RADVAGPRPCQRSLSVLSPRQPAQNRESTPLASGPSSFQRAGSVRDRVHKFTSDSP
MAARLQDGTPQAALSPLTPARLLGPSLTSTTPASSSSGSSSRGPSDTSSRFSKEQRG
VAQPLAQLRSCPQEEGPRGRGLAARPLENRAGGPVARSEEPGAPLPVAVGTAEPGG
SMKTTFTIEIKDGRGQASTGRVLLPTGNQRAELTLGLRAPPTLLSTSSGGKSTITRVNS
PGTLARLGSVTHVTSFSHAPPSSRGGCSIKMEPEPAEPLAAAVEAANGAEQTRVNKA
PEGRSPLSAEELMTIEDEGVLDKMLDQSTDFEERKLIRAALRELRQRKRDQRDKERE
RRLQEARGRPGEGRGNTATETTTRHSQRAADGSAVSTVTKTERLVHSNDGTRTART
TTVESSFVRRSENGSGSTMMQTKTFSSSSSSKKMGSIFDREDQASPRAGSLAALEKR
QAEKKKELMKAQSLPKTSASQARKAMIEKLEKEGAAGSPGGPRAAVQRSTSFGVPN
ANSIKQMLLDWCRAKTRGYEHVDIQNFSSSWSDGMAFCALVHNFFPEAFDYGQLSP
QNRRQNFEVAFSSAETHADCPQLLDTEDMVRLREPDWKCVYTYIQEFYRCLVQKGL
VKTKKS

FIG. 4

MCLRGGCSPRAPAAAPQPRPPPALPPRPRAPVPASRPGRPLLTPARPCGRMRRGS
PGPRLGGSRGERRRPAGRDPARVGPGQGLRRPARPGPAAWTETGQGIVHALTDLSI
PGMTSGNGNSASSIAGTAPQNGENKPPQAIVKPQILTHVIEGFVIQEGADVSRWDARL
LVGNLKKKYAQGFLPEKLPQQDHTTTTDSEMEEPYLQESKEEGAPLKLKCELCGRVD
FAYKFKRSKRFCSMACAKRYNVGCTKRVGLFHSDRSKLQKAGAATHNRRRPAKPVC
HHLPRIPRSSQQALCPFRLLLLCVTHSQEDSSRCSDNSSYEEPLSPISASSSTSAGDK
ASGTWSSPTCICGTWWAWDTTSCQVSHQVNVEDVYEFIRSLPGCQEIAEEFRAQEID
GQALLLLKEDHLMSVMNIKLGPALKIYARISMLKDS

FIG. 5

```
MDLLPPKPKYNPLRNESLSSLEEGASGSTPPEELPSPSASSLGPILPPLPGDDSPLPC
VPSFPRMSNLKLANPAGGPWGLKGSQERLLKMGKGVQGQPFGLRPLAPPPDMNKL
SGGGGRRTRVEGGQLGGEEWTRHGSFVNKPTRGWLHPNDKVMGPGVSYLVRYMG
CVEVLQSMRALDFNTRTQVTREAISLVCEAVPGAKGATRRRKPCSRPLSSILGRSNLK
FAGMPITLTVSTSSLNLMAADCKQIIANHHMQSISFASGGDPDTAEYVAYVAKDPVNQ
RACHILECPEGLAQDVISTIGQAFELRFKQYLRNPPKLVTPHDRMAGFDGSAWDEEE
EEPPDHQYYNDFPGKEPPLGGVVDMRLREGAARPTLPSAQMSSHLGATLPIGQHAA
GDHEVRKQMLPPPPCPGRELFDDPSYVNIQNLDKARQAGGGAGPPNPSLNGSAPRD
LFDMKPFEDALRVPPPPQSMSMAEQLQGEPWFHGKLSRREAEALLQLNGDFLVRES
TTTPGQYVLTGLQSGQPKHLLLVDPEGVVRTKDHRFESVSHLISYHMDNHLPIISAGS
ELCLQQPVDRKV
```

FIG. 6

Shc A
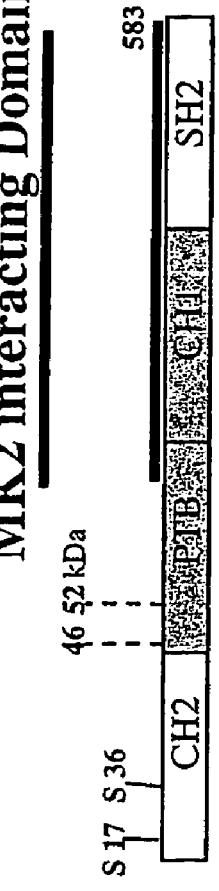
Human Polyhomeotic 2
Similar to Smoothelin
FIG. 8

Yeast Assays
| MK2 Interactor &: | Growth | | | Color | | |
|---|---|---|---|---|---|---|
| | V | K93R | L | V | K93R | L |
| Media: | -ad, -his, -leu, -trp | | | -leu, -trp, X alpha GAL | | |
FIG. 9A
Growth & Color
| Protein | V | K93R | MK2 | TPL2 Lamin |
|---|---|---|---|---|
| Shc A | - | + | + | - |
| Human Polyhomeotic 2 | - | + | + | - |
| Smoothelin Like | - | + | + | - |
FIG. 9B
MK2 Interaction Domains
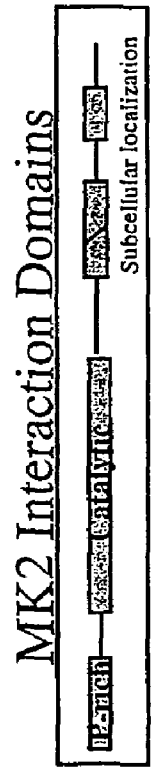
Shc A
HPH2
Smoothelin Like
FIG. 9C

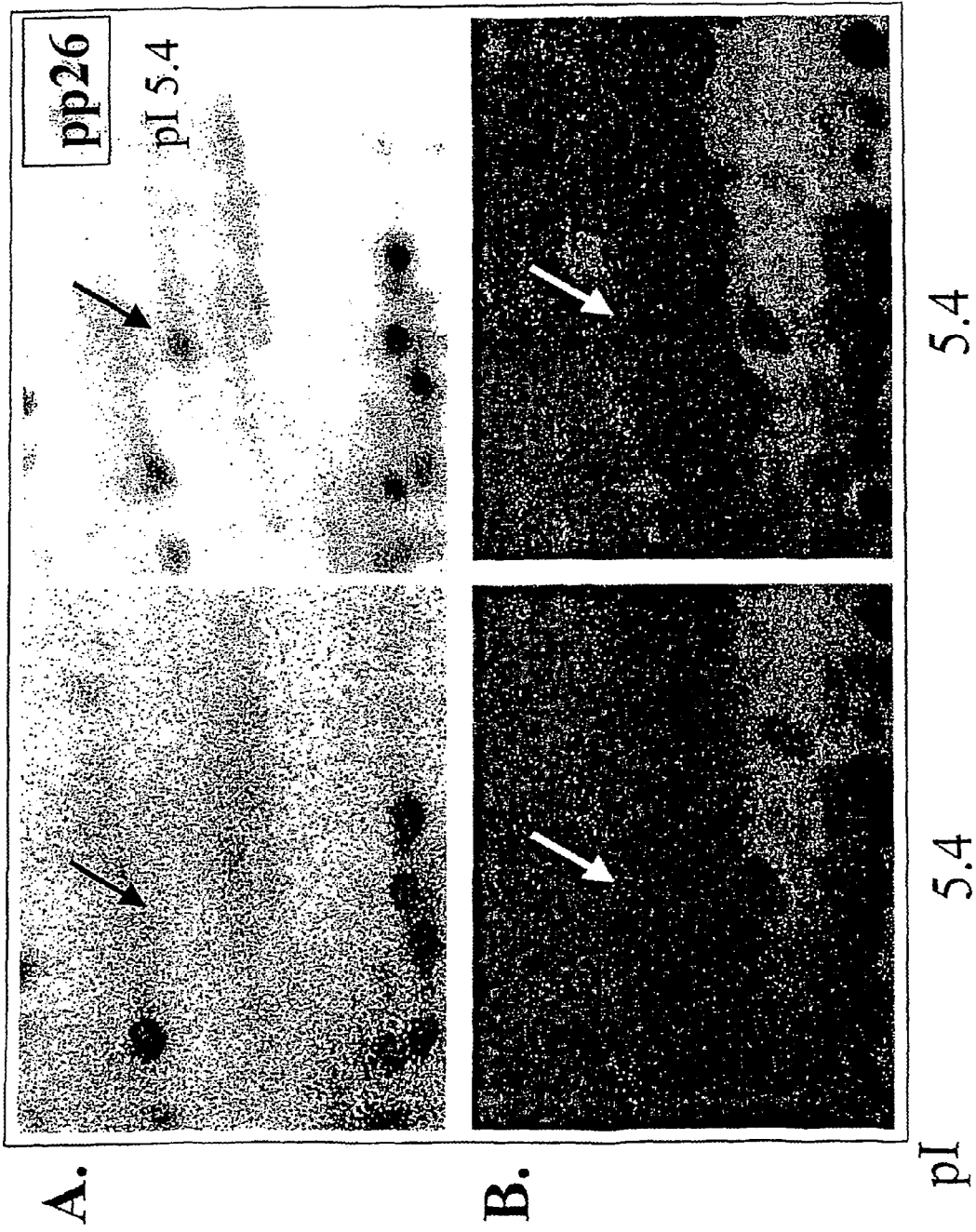

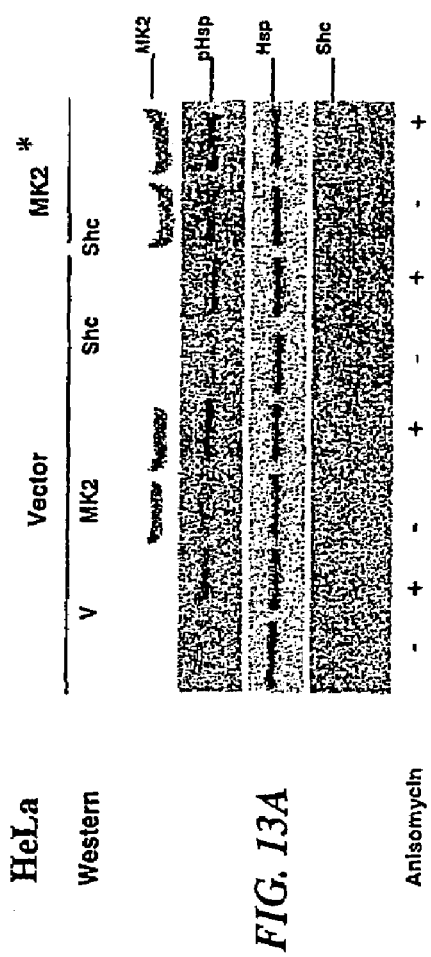
FIG. 13A
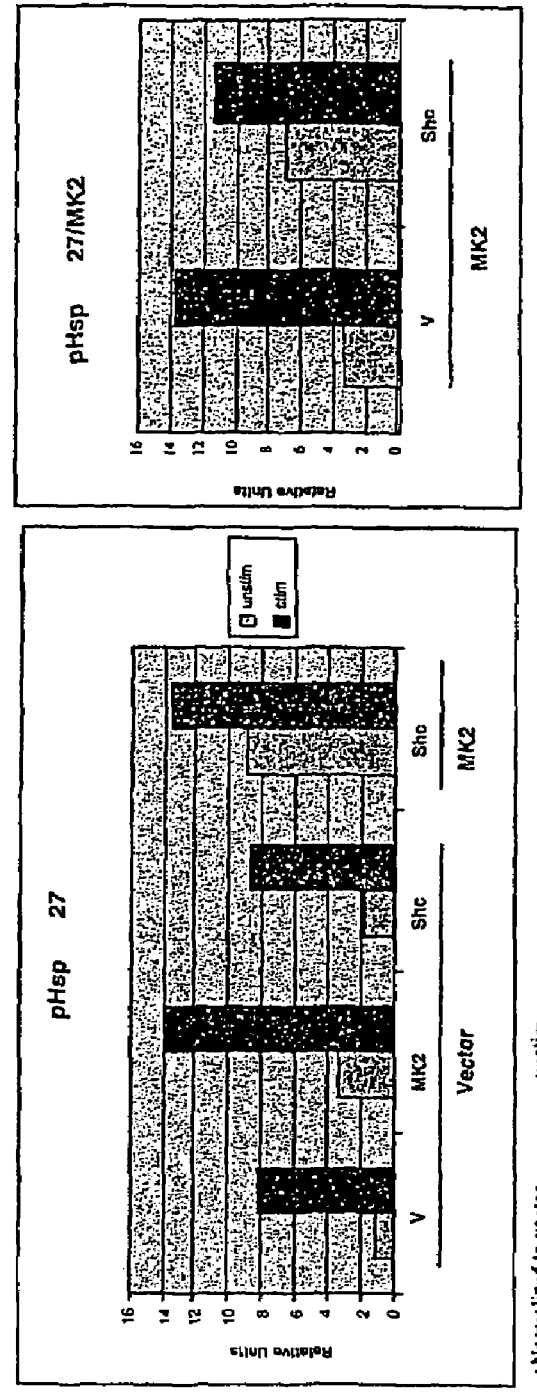
FIG. 13B
FIG. 13C

MK2 INTERACTING PROTEINS

RELATED APPLICATION

This application is a 371 of international application PCT/US03/23981, filed Aug. 1, 2003, which relies on the benefit of priority of U.S. provisional patent application Ser. No. 60/400,044 filed Aug. 2, 2002.

FIELD OF THE INVENTION

The present invention relates to uses of proteins that bind MAPKAP kinase 2 (MK2). More particularly, the invention relates to uses of proteins that bind MK2 for treating conditions that are related to inflammation. The invention is useful for treating conditions such as Crohn's disease, inflammatory bowel disease, ulcerative colitis, rheumatoid arthritis, acute respiratory distress syndrome, emphysema, delayed type hypersensitivity reaction, asthma, systemic lupus erythematosus, and inflammation due to trauma, injury or stroke.

BACKGROUND OF THE INVENTION

A number of human and animal conditions are associated with inflammation. To date, very few reliable or effective therapies exist for these conditions. However, the terrible symptoms associated with these conditions may be substantially reduced by employing therapies that decrease inflammation in patients suffering from the condition. While not curing the conditions, such therapies would significantly improve the quality of life for these patients and could ameliorate some of the effects of these conditions. Thus, there is a need in the art to identify new therapies that may contribute to an overall decrease in inflammation in patients suffering from these conditions.

Inflammatory conditions are often associated with inappropriate regulation of cytokines (Han et al., Nature Cell Biol., E39-E40 (1999)). For this reason, the selective inhibitors of inflammatory cytokine expression are potential agents for the treatment of conditions related to inflammation.

MAPKAP kinase 2 (MK2) is thought to contribute to the regulation of several cytokines and thus may be an essential component of the inflammatory response. Mice with a null mutation for MK2 show an increased resistance to lipopolysaccharide-induced endotoxic shock (Kotlyrov et al., Nature Cell Biol., 1:94-97 (1999)). This stress resistance is thought to result from the decrease in the biosynthesis of several inflammatory cytokines including TNF-α, IL-1β, IL-6, IL-10, and IFN-γ. Because of the role of MK2 in the regulation of inflammatory cytokines, proteins that bind and inhibit MK2 activity are potential agents for decreasing inflammation.

MK2 has been shown to associate with a number of proteins. MK2 is phosphorylated by p38 MAP kinase in response to certain environmental stress or inflammatory cytokines (Kotlyarov et al., Nature Cell Biology, 1:94-97 (1999)), as shown in FIG. 7. MK2 phosphorylates serum response factor (SRF) (Heidenreich et al., J. Biol. Chem., 274:14434-14443 (1999)), CREB and ER81 (Janknecht, J. Biol. Chem., 276:41856-41861 (2001)), small heat shock protein and leukocyte specific protein 1 (reviewed in Neininger et al., EMBO Reports, 2:703-708 (2001)), E47 (Neufeld et al., J. Biol. Chem., 275:20239-20242 (2000)), Akt (Rane et al., J. Biol. Chem., 276:3517-3523 (2001)), tyrosine hydroxylase, and TTP (Mahtani et al., Mol. Cell Biol., 21:6461-6469 (2001)). In addition, MK2 interacts with 5-lipoxygenase, which catalyzes important steps in the synthesis of leukotrienes, which are a group of inflammatory mediators (Janknecht, J. Biol. Chem. 276:41856-41861 (2001)). One protein hnRNP A0, however, has been shown to be differentially regulated in MK2+/+ and −/− cells.

Thus, due to MK2's involvement in inflammatory responses, it may be a desirable target for therapeutic intervention. In particular, therapeutic agents that inhibit the activity of MK2 may be used to treat human or animal conditions in which a decrease in inflammation would be therapeutically beneficial.

SUMMARY OF THE INVENTION

Accordingly, the invention relates to proteins that interact with MK2. Proteins that bind MK2, including splice variants, truncations, fragments, substitutions, addition and deletion mutations, fusion protein, shuffling mutants and motif sequences, and homologues of such proteins are potential novel anti-inflammatory drug agents.

The present invention further relates to protein complexes comprising MK2 and an MK2 interacting protein such as, for example, STS, HPH2 and Shc and variants thereof. Examples of additional MK2 interacting proteins include SRF, CREB, ER81, tyrosine hydroxylase, TTP, small heat shock protein 1, E47, Akt and 5-lipoxygenase. One or more of these proteins may also be present in a protein complex including MK2. The invention also provides methods of making and using such protein complexes for identifying potential compounds for treating conditions and diseases where modulation of inflammation is desired.

The present invention provides methods for modulating inflammatory activity in cells that express MK2. Such methods comprise administering an effective amount of a protein that binds MK2. The present invention also encompasses methods for expressing a protein in a cell by administering a DNA molecule encoding at least one protein that binds MK2.

The present invention also includes drug screening methods to identify anti-inflammatory drugs. In some embodiments, an anti-inflammatory drug is identified by a method comprising, for example, providing a complex including MK2 and at least one MK2 interacting protein, adding an effective amount of a test compound to the complex and determining whether the test compound inhibits interaction of MK2 with an interacting protein. Anti-inflammatory drugs identified by a method according to the invention include small molecules, chemical agents, proteins, peptides and antibodies which inhibit an interaction between MK2 and an MK2 interacting protein. Additionally, the present invention also provides methods of identifying potential anti-inflammatory drugs which allow an interaction between MK2 and at least one MK2 interacting protein but block MK2 activity. Examples of anti-inflammatory drugs include small molecules, chemical agents, proteins, peptides and antibodies.

According to the invention, compounds (such as proteins, peptides, antibodies, chemical agents, and small molecules) that interact with at least one of MK2 or an MK2 complex and modulate MK2 activity may be administered to a patient, in a therapeutically effective dose, in order to treat or prevent medical conditions in which a decrease in inflammation would be therapeutically beneficial. Embodiments include treatment of conditions involving cells and tissue that are associated with an increase in inflammation.

Compounds that interact with at least one of MK2 or an MK2 complex may be included in a pharmaceutical preparation. The pharmaceutical preparation may contain other components, such as agents that aid in the binding of the compound to MK2 or an MK2 complex.

In addition, compounds that interact with at least one of MK2 or an MK2 complex may be used as a diagnostic tool to quantitatively or qualitatively detect MK2. For example, these compounds may be radioactively labeled, tissue may be incubated with the labeled protein, and the excess, unbound protein may be washed away. The tissue may then be assessed for the presence of radioactive activity, which would indicate the presence of MK2. Compounds that interact with at least one of MK2 or an MK2 complex may be used to detect the presence, absence, or amount of MK2 in a cell, bodily fluid, tissue, or organism. The presence or amount of MK2 detected may be correlated with one or more of the medical conditions listed herein.

The invention also includes compounds that promote interaction between MK2 and an MK2 interacting protein, where the MK2 interacting protein stimulates MK2 activity resulting in a inflammatory response. Such agents are particularly useful in the treatment of conditions such as, for example, *Listeria monocytogenes* infection, where stimulation of MK2 and a subsequent increase in TNF-α production is desirable.

Accordingly, the invention also encompasses a kit to be used for the detection of the level of MK2 in a sample, comprising at least one compound that interacts with MK2 or an MK2 complex, whether it is labeled or unlabeled, and at least one agent that bind to this compound, such as a labeled antibody. The kit may also include the appropriate biological standards and control samples to which one could compare the results of the experimental detection. It may also include buffers or washing solutions and instructions for using the kit. Structural components may be included on which one may carry out the experiment, such as sticks, beads, papers, columns, vials, or gels.

BRIEF DESCRIPTION OF THE FIGURES

FIGS. 1A through 1B show the cDNA sequence encoding "similar to smoothelin" (STS) protein, corresponding to SEQ ID NO:1.

FIGS. 2A and 2B show the cDNA sequence encoding human polyhomeotic 2 (HPH2) protein, corresponding to SEQ ID NO:2.

FIGS. 3A and 3B show the cDNA sequence encoding a src homology and collagen (Shc) protein, corresponding to SEQ ID NO:3.

FIG. 4 shows the amino acid sequence for "similar to smoothelin" (STS) protein, corresponding to SEQ ID NO:4.

FIG. 5 shows the amino acid sequence for human polyhomeotic 2 (HPH2) protein, corresponding to SEQ ID NO:5.

FIG. 6 shows the amino acid sequence for src homology and collagen (Shc) protein, corresponding to SEQ ID NO:6.

FIG. 8 shows the structural as well as MK2 interacting domains of Shc A, HPH2, and STS. All three isoforms: 46, 52, and 66-kDa of Shc contain a src homology 2 (SH2) domain, a phosphotyrosine binding (PTB) domain, and a collagen homology domain 1, CH1. The 66 kDa isoform additionally contains a collagen homology domain 2, CH2. Human polyhomeotic 2 has a sterile alpha motif (SAM) protein interaction domain. STS contains actin binding domain (ABD) and a calponin homology domain (CH).

FIG. 9A shows growth and color of yeast on selective media in specificity assays for detecting interaction of various MK2 interacting proteins with mutant MK2 in yeast. MK2 interacting proteins, Shc, HPH2 and STS bind catalytically inactive MK2 K93R mutant. MK2 interacting proteins do not bind empty BD vector (V) or lamin (L). FIG. 9B summarizes the data obtained from the assays of FIG. 9A, where each of Shc, HPH2 and STS bind MK2 and MK2 K93R with substantially the same affinity. FIG. 9C shows domains in MK2 that interact with Shc, HPH2, and STS. The MK2 N-terminal proline rich, catalytic, and C-terminal localization domains are shown.

FIG. 10 depicts co-immunoprecipitation (IP) of proteins with MK2 in 293T cells as detected with Western blotting (WB) in presence or absence of anisomycin.

FIG. 12A depicts a 2D autoradiography showing $^{33}$P labeled proteins from MK2+/+ and MK2−/− mouse embryo fibroblasts resolved using two-dimensional gel electrophoresis. A differentially phosphorylated protein is shown (arrow) which has an isoelectric focusing point of 5.4. FIG. 12B shows silver staining of the same gel depicting the relative abundance of the resolved proteins.

FIG. 13A depicts a western blot for detecting phosphorylated Hsp 27 (pHsp 27) in the presence of MK2 or MK2 and Shc in both anisomycin stimulated and unstimulated HeLa cells. As depicted, V5-p66 Shc A and MK2 are expressed in HeLa cells and immunoblotting with an anti-pHsp 27 shows an increase in the levels of basal pHsp 27 protein in cells expressing either MK2 or MK2 and Shc. FIG. 13B depicts levels of basal phosphorylated Hsp 27 protein in HeLa cells transfected with either vector alone (V), MK2 alone, Shc alone or MK2 and Shc in both anisomycin stimulated and unstimulated HeLa cells. The levels of phosphorylated Hsp 27 protein are normalized to levels in unstimulated cells transfected with vector alone. FIG. 13C depicts levels of basal phosphorylated Hsp 27 normalized to MK2 levels in HeLa cells transfected with either MK2 and vector (V) or MK2 and Shc.

BRIEF DESCRIPTION OF THE SEQUENCES

Figure 7:
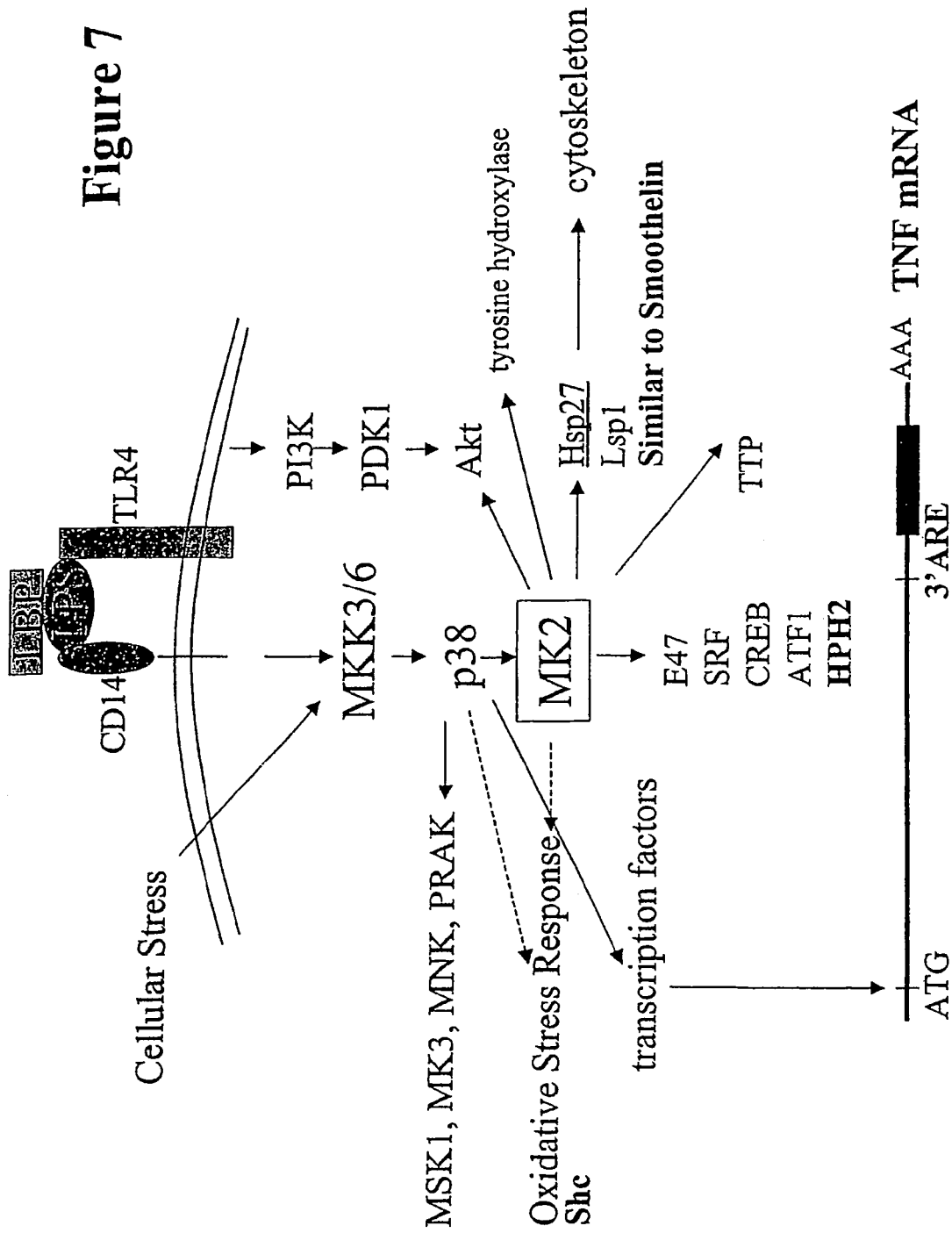
FIG. 7 shows a diagram of the p38/MK2 signalling pathway. P38 MAP kinase signaling pathways are activated in response to certain environmental stresses or pro-inflammatory cytokines. P38 is directly phosphorylated by the MKK3/6 MAP kinase kinases. Substrates of p38 include transcription factors as well as a number of kinases which amplify and diversify p38 signaling. The MK2 kinase is a p38 substrate which can phosphorylate a number of proteins including transcription factors, cytoskeletal associated proteins, and an RNA binding protein. MK2 also regulates TNF biosynthesis at a post-transcriptional level.

The following table provides information on the sequences in this application:

| Sequence ID Number | FIG. | Sequence Description |
|---|---|---|
| SEQ ID NO: 1 | 1A and 1B | cDNA sequence encoding STS |
| SEQ ID NO: 2 | 2A and 2B | cDNA sequence encoding HPH2 |
| SEQ ID NO: 3 | 3A and 3B | cDNA sequence encoding Shc |
| SEQ ID NO: 4 | 4 | Amino acid sequence of STS encoded by the cDNA sequence of SEQ ID NO: 1 |
| SEQ ID NO: 5 | 5 | Amino acid sequence of HPH2 encoded by the cDNA sequence of SEQ ID NO: 2 |
| SEQ ID NO: 6 | 6 | Amino acid sequence of Shc encoded by the cDNA sequence of SEQ ID NO: 3 |

Definitions

The term "complex" refers to an association of two or more proteins. Such an association may either be covalent or non-covalent including, for example, ionic, hydrophilic and hydrophobic interactions between two proteins in a complex. Typically, proteins that form a complex interact with each other such that identification or detection of a first protein in the complex leads to identification or detection of other protein or proteins that form a complex with the first protein. A protein complex can either be identified in vivo, where two or more proteins naturally associate with each other, for example, in a cell to form a complex. Alternatively, a complex can be formed in vitro, where an interaction between two or more proteins occurs when these proteins are added to a same reaction mixture. Methods that are used for detection of proteins in a complex include, but are not limited to, co-immunoprecipitation, yeast two-hybrid, fluorescence resonance energy transfer and pull-down assays. An MK2 complex is a complex that contains MK2 and at least one other protein.

The term "co-immunoprecipitation" refers to a method for detecting an interaction between two proteins. For example, interaction between an HA-tagged MK2 interacting protein such as Shc, and MYC-tagged MK2 co-expressed in 293T cells can be detected by immunoprecipitation. Cell lysates are prepared from cells co-expressing both proteins that are subsequently immunoprecipitated with an anti-HA antibody. Immunoprecipitates are resolved by SDS PAGE and immunoblotted with an anti-MYC antibody to detect co-immunoprecipitated MK2.

The term "HPH2" refers to human polyhomeotic homolog 2, which is one of the polycomb group (PcG) of proteins and has a molecular weight of approximately 51 kDa. HPH2 interacts with MK2 to form a complex, thereby modulating MK2 activity. The term "HPH2" also includes variants of HPH2 including splice variants, homologues, fusion proteins including HPH2, truncation and deletion mutants, fragments, substitution mutants, addition mutants, shuffling mutants and motif sequences of HPH2, which interact with MK2. Thus the term "HPH2" further refers to functional variants of HPH2, including fragments of HPH2, which interact with MK2. HPH2 is homologous to the *Drosophila melanogaster* PcG protein 'polyhomeotic' as well as to the mouse Rae28/Mph1 protein (Gunster et al., Molec. Cell. Biol., 17: 2326-2335 (1997)). In *Drosophila,* the PcG genes are part of a cellular memory system that is responsible for the stable inheritance of gene activity. PcG proteins form a large multimeric, chromatin-associated protein complex and contain a zinc finger motif and two regions designated homology domains I and II. These complexes maintain transcriptional silencing/activation during development and maintain transcriptional memory during the cell cycle, especially cell division. Mutations in the PcG genes are associated with proliferation defects in hematopoietic cells, implicating these proteins in regulation of hematopoiesis. The cDNA sequence for HPH2 is provided in FIGS. 2A and 2B (corresponding to SEQ ID NO:2) and the amino sequence of the protein is provided in FIG. 5 (corresponding to SEQ ID NO:5). FIG. 8B shows the structure of HPH2 and the MK2 interacting domain in HPH2, and FIG. 9C illustrates the HPH2 interacting domain in MK2. HPH2 has a conserved C terminal sterile alpha motif (SAM) protein interaction domain found in a number of signaling proteins including kinases, scaffolding proteins, adaptor proteins and GTPAses as well as members of the ETS family of transcription factors. It is believed that HPH2 is a transcriptional regulator.

The term "inflammation" refers to a fundamental pathologic process consisting of a dynamic complex of cytologic and histologic reactions that occur in the affected blood vessels and surrounding tissues in response to an injury or abnormal stimulation caused by a physical, chemical, or biological agent.

The term "inflammatory condition" refers to conditions in which inflammation is a symptom. Such conditions include, but are not limited to Crohn's disease, inflammatory bowel disease, ulcerative colitis, rheumatoid arthritis, acute respiratory distress syndrome, emphysema, delayed type hypersensitivity reaction, asthma, systemic lupus erythematosus, and inflammation due to trauma injury or stroke such as ischemia brain injury.

The terms "MK2" and "MK2 polypeptide" refer to MAP-KAP kinase 2, a protein described in Stokoe et al. (Biochem. J. 296: 843-849 (1993)). This protein is a Ser/Thr kinase originally identified as a hsp25/27 kinase. This protein kinase has been shown to be active after phosphorylation by p38 mitogen-activated protein kinase (p38 MAP kinase). MK2 is thought to regulate TNF post-transcriptionally, and may be important in the regulation of other cytokines. Analysis of the cDNA sequence for MK2 revealed the following features (in 5' to 3' order): a proline-rich region containing 2 putative SH3-binding sites, a kinase catalytic domain, a threonine residue phosphorylated by MAP kinase, and a nuclear localization signal. MK2−/− knockout mice are viable, however there is a 90% reduction in LPS-induced TNF-α biosynthesis and these mice are resistant to LPS-induced shock. The term "MK2" further includes variants of MK2 including splice variants, homologues, fusion proteins including MK2, truncation and deletion mutants, fragments, substitution mutants, addition mutants, shuffling mutants and motif sequences of MK2, where these variants have MK2 activity. This term encompasses functional variants of MK2, where a variant MK2 protein or a fragment thereof, has an MK2 activity, as measured by one or more assays described herein and those that are known in the art.

The terms "protein that binds MK2" and "MK2 interacting protein" refer to proteins that cohere or associate with MK2. The term encompasses proteins that are found in a complex with MK2. The term also refers to any variants of such proteins (including splice variants, truncations, fragments, substitutions, addition and deletion mutations, fusion proteins, shuffling sequences and motif sequences, and homologues) that have one or more of biological activities associated with native proteins. These proteins further include amino acid sequences that have been modified with conservative or non-conservative changes to the native proteins. These proteins may be derived from any source, natural or synthetic. The protein may be human or derived from animal sources, including bovine, chicken, murine, rat, porcine, ovine, turkey, baboon, and fish. A protein that binds MK2 may stimulate MK2, inhibit MK2, or have no effect on MK2 activity.

The term "Shc" refers to src homology and collagen (Migliaccio et al., Nature, 402:309-313 (1999)). The term "Shc" further includes variants of Shc including splice variants, homologues, fusion proteins including Shc, truncation and deletion mutants, fragments, substitution mutants, addition mutants, shuffling mutants and motif sequences of Shc, which interact with MK2. This term encompasses functional variants of Shc, where a variant Shc protein interacts with MK2, thereby modulating MK2 activity. The cDNA sequence for a Shc protein (Shc A) is provided in FIGS. 3A and 3B (corresponding to SEQ ID NO:3) and the amino sequence of the protein is provided in FIG. 6 (corresponding to SEQ ID NO:6). FIGS. 8A and 16A show various domains in a Shc protein, including CH2, PTB, CH1, SH2, and the MK2 interacting domain. FIG. 9C shows the domain in MK2 which interacts with Shc. Three isoforms: 46, 52, and 66-kDa of the Shc A protein are phosphorylated after engagement with cell surface receptors. The two smaller isoforms are generated through different translation initiation while the 66 kDa isoform, which has a unique N terminal CH domain (CH2), is generated through alternative splicing. Src homology 2 (SH2) and phosphotyrosine binding (PTB) domains bind phosphotyrosine on activated cell surface receptors, resulting in tyrosine phosphorylation of the CH 1 domain, which promotes recruitment of Grb2 and SOS. Many activated cell surface receptors signal through the two smaller Shc A Isoforms to activate the Ras MAP kinase pathway. In contrast, p66 binding to these receptors has not been shown to activate this mitogenic pathway. The collagen homology 2 (CH2) domain is unique to p66 and contains serine 36, which is phosphorylated upon oxidative stress. The mammalian isoforms of Shc regulate functions as diverse as growth (p52/p46Shc), apoptosis (p66Shc), and life-span (p66Shc) (Luzi et al., Curr. Opin. Genetics and Development, 10:668-674 (2000)).

It is believed that Shc A is a signaling adapter phospho protein. The p46 and p52 isoforms of the Shc A protein are ubiquitously expressed with the exception of the brain and neurons, where they are developmentally regulated. p66 is expressed in specific cell types and tissues. Because p66 does not activate the Ras MAPK pathway, its binding, which is proposed to compete with that of the two smaller Shc A isoforms, is thought to modulate activation of the Ras MAPK pathway through its differential expression. It has been shown in cells isolated from p66−/− mice that p66 acts downstream of p53 to mediate cellular responses to oxidative stress including intracellular ROS and apoptosis. Phosphorylation of a serine residue at position 36 in the p66 isoform (S36) is required for this activity. Two MAP kinases: Erk and Jnk have been implicated in phosphorylating this serine.

The term "similar to smoothelin" or "STS" refers to a specific protein closely related to smoothelin. The term "STS" further includes variants of STS including splice variants, homologues, fusion proteins including STS, truncation and deletion mutants, fragments, substitution mutants, addition mutants, shuffling mutants and motif sequences of STS, which interact with MK2. This term encompasses functional variants of STS, where a variant STS protein interacts with MK2. STS has not been fully characterized, however the predicted cDNA for STS is documented in the National Center for Biotechnology Information (NCBI) data base, National Institutes of Health, and its predicted molecular weight is 100 kDa. STS is 94% identical to smoothelin and both proteins have a calponin homology and an actin binding domain based on sequence homology with known proteins in the NCBI database. These proteins contain an actin binding domain (ABD) and a calponin homology domain (CH). van der Loop et al., J. Cell Biol., 134: 401-411 (1996) determined that smoothelin has significant homology to a sequence that flanks the actin-binding domains of dystrophin, utrophin, beta-spectrin, and alpha-actinin. Cell fractionation studies suggested to the authors that smoothelin is a part of the cytoskeleton. Northern blot analysis revealed that the gene is expressed in several tissues containing vascular smooth muscle, but not in brain, adipose tissue, cardiac muscle, or skeletal muscle. The expression pattern of STS has yet to be determined. The cDNA sequence encoding STS is provided in FIGS. 1A-1B (corresponding to SEQ ID NO:1) and the amino sequence of the protein is provided in FIG. 4 (corresponding to SEQ ID NO:4). The structure of STS protein, including the MK2 binding region, is shown in FIG. 8C. It has a C terminal actin binding domain (ABD) and a calponin homology domain (CH). FIG. 9C shows the domain in MK2 that interacts with STS. It is believed that STS is a cytoskeletal associated protein.

The term "therapeutic benefit" refers to an improvement in symptoms of a condition, a slowing of the progression of a condition, or a cessation in the progression of a condition. The therapeutic benefit is determined by comparing an aspect of a condition, such as the amount of inflammation, before and after administration of at least one protein that binds MK2. Therapeutic benefit can also be determined by comparing an aspect of a condition, such as the amount of inflammation, before and after administration of at least one agent that inhibits interaction of MK2 with a protein, where the interaction stimulates MK2 activity. Additionally, therapeutic benefit can also be determined by comparing an aspect of a condition, before and after administration of at least one agent that promotes the interaction between MK2 and a protein, where the interaction inhibits MK2 activity.

In case of certain conditions, however, such as certain bacterial infections, for example, Listeria monocytogenes infection, it is desirable to have an enhanced MK2 activity. Accordingly, therapeutic benefit can also be determined by an increased resistance to such an infection, before and after administration of an agent that enhances MK2 activity or promotes the interaction between MK2 and a protein, where the interaction enhances MK2 activity, resulting in, for example, increased resistance to bacterial infection.

The terms "treat", "treating" and "treatment" refer to both therapeutic treatment and prophylactic or preventative treatment. Those in need of treatment may include individuals already having a particular medical condition as well as those who may ultimately acquire the condition (i.e., those who are susceptible to the condition and thus needing preventative measures). For example, these terms encompass any treatment which leads to a reduction in severity of a disease or condition, reduction in the duration of the disease course, amelioration of one or more symptoms associated with a disease or condition, beneficial effects to the patient with a disease or condition, without necessarily curing the disease or condition and prophylaxis of one or more symptoms associated with a disease or condition.

The term "domain" as used herein means a region of a polypeptide (including proteins) having some distinctive physical feature or role including, for example, an independent structure or a function. Domains refer to a portion of a polypeptide that may be either native or non-native to the polypeptide. A domain may contain the amino acid sequence with a distinctive physical feature or it may contain a fragment of the sequence. A domain may interact with other domains within a polypeptide or protein. In some embodiments of the invention, an MK2 polypeptide and/or an MK2 interacting protein includes a domain chosen from affinity tags, radionucleotides, enzymes and fluorophores. Such a domain can be used for isolation or purification of a complex including MK2 and an interacting protein or for isolation of a protein that includes the domain. Examples of domains include, but are not limited to, polyhistidine, FLAG, Glu-Glu, glutathionine S transferase (GST), thioredoxin, protein A, protein G, and an immunoglobulin heavy chain constant region.

The term "fusion protein" refers to a protein where a first amino acid sequence derived from a first source is linked, covalently or non-covalently, to a second amino acid sequence derived from a second source, wherein the first and second amino acid sequences are not the same. A first source and a second source that are not the same can include two different biological entities, or two different proteins from the same biological entity, or a biological entity and a non-biological entity. A fusion protein can include for example, a protein derived from at least 2 different biological sources. A biological source can include any non-synthetically produced nucleic acid or amino acid sequence (e.g. a genomic or cDNA sequence, a plasmid or viral vector, a native virion or a mutant or analog, as further described herein, of any of the above). A synthetic source can include a protein or nucleic acid sequence produced chemically and not by a biological system (e.g. solid phase synthesis of amino acid sequences). A fusion protein can also include a protein derived from at least 2 different synthetic sources or a protein derived from at least one biological source and at least one synthetic source.

The term "isolated" in reference to a protein or a polypeptide refers to a protein or polypeptide separated from its natural or native environment or source. Thus, a protein or polypeptide isolated from a cell is prepared substantially free of other polypeptides and components in the cell.

The term "recombinant" as used herein refers to a polypeptide, which by virtue of its origin or manipulation is not associated with all or portion of a polypeptide with which it is naturally associated in nature or where such a polypeptide does not naturally occur in nature.

The term "Y2H" refers to the yeast two-hybrid system of detecting interactions between two proteins. The two hybrid uses the yeast transcriptional activator: GAL4, divided into two functionally distinct domains. The DNA binding domain which when fused to a heterologous protein X retains its DNA binding activity, and the activation domain which retains its transcriptional activation properties when fused to a heterologous protein Y. The two fusion or hybrid proteins are co-expressed in yeast. If there is an interaction between protein X and protein Y, the association will bring the activation domain of the transcriptional activator into close association with its binding domain, thereby reconstituting a functional transcriptional activator. This reconstituted transcriptional activator can then drive the expression of a number of reporter genes, integrated into the yeast genome, which contain the binding site for the DNA binding domain. Reporter gene expression is indicative of an interaction between protein X and protein Y.

DETAILED DESCRIPTION OF THE INVENTION

A. MK2 Interacting Proteins

The present invention relates to proteins that interact with MK2. Examples of proteins known to interact with MK2 include, but are not limited to SRF, CREB, ER81, small heat shock protein, leukocyte specific protein 1, E47, Akt, and 5-lipoxygenase.

HPH2 has previously been shown to bind MK2 by a Y2H system assay (B. Neufield, Neue Interaktionspartner der MAPKAP-Kinasen 3 pK und MK2: die Polycomb-Proteine HPH2 und Bmi1 sowie der basische Helix-Loop-Helix-Transkriptionsfaktor E47 (2000) (unpublished Ph.D. dissertation, University of Würzburg). This finding was confirmed in the present invention (FIGS. 2A and 2B, FIG. 9B and Example 5). In addition, STS (FIGS. 1A to 1B, FIG. 9B and Example 5) and Shc (FIGS. 3A and 3B, FIG. 9B and Example 5) are shown to bind MK2 using the Y2H system in the present invention.

Proteins that bind MK2, may be isolated using a variety of methods. For example, one may use co-immunoprecipitation, as exemplified in Example 7. A V-5 or HA-tagged MK2 interacting protein, and MYC-tagged MK2 were co-expressed in cells. Lysates of the cells were prepared and immunoprecipitated with an anti-HA or anti-V5 antibody. Immunoprecipitates were resolved by SDS PAGE and immunoblotted with an anti-MYC antibody to detect co-immunoprecipitated MK2.

One could also use the yeast two-hybrid (Y2H) system, as exemplified in Examples 1-5. This method was first formally described by Fields and Song. (Nature, 340:245-246 (1989)). The two hybrid system uses a yeast transcriptional activator, such as GAL4, divided into 2 functionally distinct domains. The GAL4 DNA binding domain retains its DNA binding activity when fused to a heterologous protein X. The GAL4 activation domain retains its transcriptional activation properties when fused to a heterologous protein Y. The two fusion or hybrid proteins are co-expressed in yeast. If there is an interaction between protein X and protein Y, the association will bring the activation domain of GAL4 into close association with its binding domain, thereby reconstituting a functional transcriptional activator. This reconstituted transcriptional activator can then drive the expression of a number of reporter genes, integrated into the yeast genome, which contain the binding site for the DNA binding domain. Thus, reporter gene expression is indicative of an interaction between protein X and protein Y.

The Y2H system offers several advantages over more traditional methods for studying protein-protein interactions (Luban et al., Curr. Opin. Biotech., 6:59-64 (1995)). First, the detailed and laborious manipulation of the conditions necessary for in vitro biochemical binding assays is not needed since the interaction occurs in vivo. Second, the Y2H system is highly sensitive, and can detect interactions not revealed by other methods (Fields et al., Trends in Genetics, 10:286-291 (1994)). Finally, the Y2H system is particularly powerful when it is used to screen a cDNA library for encoded proteins that interact with a protein of interest.

In addition to the Y2H system, a mammalian 2-hybrid system can also be used for studying the interaction between MK2 and another protein. For example, 293T cells can be transfected with: a plasmid containing a DNA sequence that binds GAL4 upstream of a reporter gene such as luciferase or chloremphenicol acetyl transferase (CAT); a plasmid containing cDNA encoding MK2 fused to the DNA-binding domain of GAL4; and a plasmid containing cDNA encoding a protein that interacts with MK2, as identified via Y2H, or a putative MK2 interacting protein, fused to the VP16 activator. Transfected cells are lysed subsequent to co-expression of MK2 and the interacting protein and the lysates are assayed for reporter gene activity, which would be detected only when MK2 interacts with the protein. By this assay, the interaction between MK2 and a protein can be confirmed in mammalian cells. The mammalian two-hybrid system can also be used to validate the interaction between MK2 and another protein, as identified via the Y2H system.

In addition to using co-immunoprecipitation or two-hybrid systems, one may use a low stringency screening of a cDNA library, or use degenerate PCR techniques using a probe directed toward a sequence encoding a MK2 binding domain of a protein that binds MK2. As more genomic data becomes available, similarity searching using a number of sequence profiling and analysis programs, such as Motif-Search (Genetics Computer Group, Madison, Wis.), ProfileSearch (GCG), and BLAST (NCBI) could be used to find novel proteins containing sequences significant homology with MK2 binding domains of proteins that bind MK2.

One may also use a proteomics approach to identify MK2 interacting proteins, as shown in Example 11. Wild type (+/+) or MK2 deficient (−/−) cells were plated and labeled with $^{33}$P. MK2 was activated for 30 minutes following which whole cell lysate were prepared and analyzed using two-dimensional gel electrophoresis. Gels were compared to identify differentially phosphorylated proteins. FIG. 12 shows a differentially phosphorylated protein (arrow) using this approach. Differentially phosphorylated proteins may also be identified using mass spectrometry.

A protein that binds MK2 may stimulate MK2, inhibit MK2, or have no effect on MK2 activity. There are several ways to investigate whether a protein that binds MK2 causes an inhibition or stimulation of MK2, thus having biological activity. Proteins that bind MK2 that render a change in MK2 activity, particularly a decrease in MK2 activity, are particularly good candidates for use as therapeutic agents and as inhibitors of inflammation. In addition, a fragment or mutant of a protein that naturally stimulates MK2 may be found to inhibit MK2, and would thus be a candidate as an inhibitor of inflammation. For example, once a protein that binds MK2 is identified and it is shown to stimulate MK2, mutations in the protein can be made, such that the protein still interacts with MK2 but has an inhibitory effect on MK2 activity. Mutant forms of an MK2 interacting protein can be tested for an effect on MK2 activity in one or more of the assays provided herein. Proteins that bind MK2 but have no effect on its activity can also be used as therapeutic agents. Such proteins may, for example, compete with endogenous proteins that normally bind MK2 to stimulate MK2 activity.

To investigate whether a protein that binds MK2 affects its activity, one could determine the effect of the binding proteins on MK2 activity such as; for example, MK2 kinase activity. For example, an HA-tagged MK2 interacting protein (for example, Shc), and Myc-tagged MK2 can be co-expressed in 293T cells. Cell lysates are prepared and resolved by SDS PAGE. Subsequent immunoblotting with an antibody to detect activated MK2 (for example, anti-phospho MK2 threonine 334), will determine the activation state of MK2. Alternatively, the effect of the MK2 binding on MK2 kinase activity can be determined by quantitating the amount of phosphorylated form of a known substrate for MK2.

In addition, one could determine the effect of an MK2 interacting protein on TNF-α biosynthesis, as exemplified in Example 9. An HA-tagged MK2 interacting protein (for example, Shc), and MYC-tagged MK2 can be co-transfected into appropriate cells such as RAW, along with a TNF luciferase reporter gene. Cells are either unstimulated or stimulated by anisomycin. Media is collected to assay for TNF-production and cell lysates are prepared to determine luciferase activity. TNF biosynthesis in the presence of an MK2 binding protein is compared to that in a control sample.

As exemplified in Example 10, one could also determine the effect of MK2 on the phosphorylation state of an MK2 interacting protein. An HA-tagged MK2 interacting protein (for example, Shc) is expressed in 293T cells. Lysates are prepared and immunoprecipitated with an anti-HA antibody. The immunoprecipitates are used in an in vitro kinase assay with recombinant MK2 as the kinase. SDS PAGE followed by phospho-imagery is used to detect phosphorylation of the MK2 interacting protein.

B. Nucleotide and Protein Sequences

While not always necessary, if desired, one of ordinary skill in the art may determine the amino acid or nucleic acid sequences of novel proteins that bind MK2. For example, the present invention provides the cDNA sequences encoding STS, HPH2, and Shc (FIGS. 1A and 1B; 2A and 2B; 3A and 3B; and SEQ ID NOS: 1-3). The present invention also provides the corresponding amino acid sequences of these proteins (FIGS. 4-6; SEQ ID NOS: 4-6).

The present invention also includes splice variants, truncations, fragments, substitutions, additions or deletion mutations, fusion proteins, shuffling mutants, motif sequences, and homologues of such nucleic and amino acid sequences. For example, the nucleic or amino acid sequence may comprise a sequence at least 70% to 79% identical to the nucleic acid or amino acid sequence of the native protein, or at least 80% to 89% identical, or at least 90% to 95% identical, or at least 96% to 100% identical. One of skill in the art will recognize that the region that binds MK2 can tolerate less sequence variation than the other portions of the protein not involved in binding. Thus, these non-binding regions of an MK2 interacting protein may contain substantial variations without significantly altering the binding of the protein to MK2. However, one of skill in the art will also recognize that many changes can be made to specifically increase the affinity of the protein for its target. Such affinity-increasing changes are typically determined empirically by altering the amino acid sequence, for example, within the MK2-binding region, and testing the ability of the protein to bind MK2 or by determining the strength of such binding. All such alterations, whether within or outside a MK2 binding region within a protein, are included in the scope of the present invention.

One of skill in the art will recognize that proteins that bind MK2 may contain any number of conservative changes to their respective amino acid sequences without altering their biological properties. Such conservative amino acid modifications are based on the relative similarity of the amino acid side-chain substituents, for example, their hydrophobicity, hydrophilicity, charge, size, and the like. Exemplary conservative substitutions which take such characteristics into consideration are well known to those of skill in the art and include, for example, arginine to lysine or lysine to arginine; glutamate to aspartate or aspartate to glutamate; serine to threonine or threonine to serine; glutamine to asparagine or asparagine to glutamine; valine to leucine or isoleucine, leucine to valine or isoleucine, and isoleucine to valine or leucine. Furthermore, proteins that bind MK2 may be used to generate functional fragments that bind and inhibit MK2 activity.

Relative sequence similarity or identity may be determined using the "Best Fit" or "Gap" programs of the Sequence Analysis Software Package™ (Version 10; Genetics Computer Group, Inc., University of Wisconsin Biotechnology Center, Madison, Wis.). "Gap" utilizes the algorithm of Needleman and Wunsch (Needleman and Wunsch, 1970) to find the alignment of two sequences that maximizes the number of matches and minimizes the number of gaps. "BestFit" performs an optimal alignment of the best segment of similarity between two sequences. Optimal alignments are found by inserting gaps to maximize the number of matches using the local homology algorithm of Smith and Waterman (Smith and Waterman, J Theor Biol., 91(2):379-80 (1981)).

The Sequence Analysis Software Package described above contains a number of other useful sequence analysis tools for identifying homologues of the presently disclosed nucleotide and amino acid sequences. For example, the "BLAST" program (Altschul et al., J Mol Biol., 215(3):403-10 (1990)) searches for sequences similar to a query sequence (either peptide or nucleic acid) in a specified database (e.g., sequence databases maintained at the NCBI; "FastA" (Lipman and Pearson, Science, 227(4693):1435-41 (1985); Pearson and Lipman, Proc. Natl. Acad. Sci. USA, (8):2444-8 (1988)) performs a Pearson and Lipman search for similarity between a query sequence and a group of sequences of the same type (nucleic acid or protein); "TfastA" performs a Pearson and Lipman search for similarity between a protein query sequence and any group of nucleotide sequences (it translates the nucleotide sequences in all six reading frames before performing the comparison); "FastX" performs a Pearson and Lipman search for similarity between a nucleotide query sequence and a group of protein sequences, taking frameshifts into account. "TfastX" performs a Pearson and Lipman search for similarity between a protein query sequence and any group of nucleotide sequences, taking frameshifts into account (it translates both strands of the nucleic sequence before performing the comparison).

The invention encompasses fragments of proteins that bind MK2. Such fragments will likely include all or a part of an MK2 binding region in the protein. Fragments may include all, a part, or none of the sequences between the region that binds MK2 and the N-terminus of the protein and/or between the region that binds MK2 and the C-terminus of the protein.

It is understood by one of ordinary skill in the art that certain amino acids may be substituted for other amino acids in a protein without adversely affecting the activity of the protein, e.g., binding characteristics of a protein that binds MK2. It is thus contemplated by the inventors that various changes may be made in the amino acid sequences of proteins that bind MK2, or DNA sequences encoding the proteins, without appreciable loss of their biological utility or activity. Such changes may include splice variants, truncations, fragments, substitution, addition and deletion mutations, shuffling mutations, motif sequences, fusion proteins, homologues, and the like.

In making such changes, the hydropathic index of amino acids may be considered. The importance of the hydropathic amino acid index in conferring a biological function of a protein is generally understood in the art (Kyte and Doolittle, J. Mol. Biol., 157: 105-132 (1982)). It is accepted that the relative hydropathic character of an amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics; these are isoleucine (+4.5), valine (+4.2), leucine (+3.8), phenylalanine (+2.8), cysteine/cystine (+2.5), methionine (+1.9), alanine (+1.8), glycine (−0.4), threonine (−0.7), serine (−0.8), tryptophan (−0.9), tyrosine (−1.3), proline (−1.6), histidine (−3.2), glutamate (−3.5), glutamine (−3.5), aspartate (−3.5), asparagine (−3.5), lysine (−3.9), and arginine (−4.5). In making such changes, the hydropathic indices of substituted amino acids may be within ±2, within ±1, and within ±0.5 of the amino acids that are replaced.

It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0), lysine (+3.0), aspartate (+3.0±1), glutamate (+3.0±1), serine (+0.3), asparagine (+0.2), glutamine (+0.2), glycine (0), threonine (−0.4), proline (−0.5±1), alanine (−0.5), histidine (−0.5), cysteine (−1.0), methionine (−1.3), valine (−1.5), leucine (−1.8), isoleucine (−1.8), tyrosine (−2.3), phenylalanine (−2.5), and tryptophan (−3.4). In making such changes, the hydropathic indices of substituted amino acids may be within ±2, within ±1, and within ±0.5 of the amino acids that are replaced.

The modifications may be conservative such that the structure or biological function of the protein is not affected by the change. Such conservative amino acid modifications are based on the relative similarity of the amino acid side-chain substituents, for example, their hydrophobicity, hydrophilicity, charge, size, and the like. Exemplary conservative substitutions which take various of the foregoing characteristics into consideration are well known to those of skill in the art and include for example, arginine to lysine or lysine to arginine; glutamate to aspartate or aspartate to glutamate; serine to threonine or threonine to serine; glutamine to asparagine or asparagine to glutamine; valine to leucine or isoleucine, leucine to valine or isoleucine, and isoleucine to valine or leucine. Amino acid sequences of proteins that bind MK2 may be modified to have any number of conservative changes, so long as the binding of the protein to MK2 is not adversely affected. Such changes may be introduced within or outside of a portion of the protein that binds the target. For example, changes introduced within the binding portion of the protein may be designed to increase the affinity of the protein for its target.

C. Stabilizing Modification

Stabilizing modifications are capable of stabilizing a protein, enhancing the in vitro and/or in vivo half life of a protein, enhancing circulatory half life of a protein and/or reducing proteolytic degradation of a protein. Such stabilizing modifications include but are not limited to fusion proteins, modification of a glycosylation site, and modification of carbohydrate moiety. As it is well known in the art, fusion proteins are prepared such that a second protein is fused in frame with the a first protein resulting in a translated protein comprising both the first and second proteins. For example, in the present invention, a fusion protein may be prepared such that a protein that binds MK2 is fused to a second protein (e.g. a stabilizer protein portion). As will be recognized by one of ordinary skill in the art, such a fusion protein may optionally comprise a linker peptide between the protein that binds MK2 and the stabilizing protein portion. A stabilizer protein may be any protein that enhances the overall stability of the protein that binds MK2.

Proteins that bind MK2 can be glycosylated or be linked to albumin or a nonproteinaceous polymer. For instance, proteins that bind MK2 may be linked to one of a variety of nonproteinaceous polymers, e.g., polyethylene glycol, polypropylene glycol, or polyoxyalkylenes, in the manner set forth in U.S. Pat. Nos. 4,640,835; 4,791,192; or 5,414,135. Proteins are chemically modified by covalent conjugation to a polymer to increase their circulating half-life, for example. Polymers, and methods to attach them to peptides, are also shown in U.S. Pat. Nos. 4,766,106 and 4,609,546.

Proteins that bind MK2 can be stabilized by preparing a fusion protein comprising a protein that binds MK2 and an immunoglobulin sequence, as exemplified in U.S. Pat. No. 5,864,020. The immunoglobulin sequence preferably, but not necessarily, is an immunoglobulin constant domain. The immunoglobulin moiety in the chimeras of the present invention may be obtained from IgG-1, IgG-2, IgG-3 or IgG-4 subtypes, IgA, IgE, IgD or IgM, but preferably IgG-1 or IgG-3. In one embodiment, the Fc fragment of IgG fused to the protein that binds MK2.

Proteins that bind MK2 may be pegylated. Pegylation is a process whereby polyethylene glycol (PEG) is attached to a protein in order to extend the half-life of the protein in the body. Pegylation of proteins that bind MK2 may decrease the dose or frequency of administration of the proteins needed for an optimal decrease in inflammation. Reviews of the technique are provided in Bhadra et al., Pharmazie, 57: 5-29 (2002), and in Harris et al., Clin. Pharmacokinet., 40: 539-551 (2001).

Proteins that bind MK2 may be modified to have an altered glycosylation pattern (i.e., altered from the original or native glycosylation pattern). As used herein, "altered" means having one or more carbohydrate moieties deleted, and/or having at least one glycosylation site added to the original protein.

Glycosylation of proteins is typically either N-linked or O-linked. N-linked refers to the attachment of the carbohydrate moiety to the side chain of an asparagine residue. The tripeptide sequences, asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to proteins that bind MK2 is conveniently accomplished by altering the amino acid sequence of the protein such that it contains one or more of the above-described tripeptide sequences (for N-linked glycosylation sites). The alteration may also be made by the addition of, or substitution by, one or more serine or threonine residues in the sequence of the original protein (for O-linked glycosylation sites). The protein's amino acid sequence may also be altered by introducing changes at the DNA level.

Another means of increasing the number of carbohydrate moieties on proteins is by chemical or enzymatic coupling of glycosides to the amino acid residues of the protein. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, CRC Crit. Rev. Biochem., 22: 259-306 (1981).

Removal of any carbohydrate moieties present on proteins that bind MK2 may be accomplished chemically or enzymatically. Chemical deglycosylation requires exposure of the protein to trifluoromethanesulfonic acid, or an equivalent compound. This treatment results in the cleavage of most or all sugars except the linking sugar (N-acetylglucosamine or N-acetylgalactosamine), leaving the amino acid sequence intact.

Chemical deglycosylation is described by Hakimuddin et al., Arch. Biochem. Biophys., 259: 52 (1987); and Edge et al., Anal. Biochem., 118: 131 (1981). Enzymatic cleavage of carbohydrate moieties on proteins can be achieved by the use of a variety of endo- and exo-glycosidases as described by Thotakura et al., Meth. Enzymol., 138: 350 (1987).

Proteins that bind MK2 may be linked to the protein albumin or a derivative of albumin. Methods for linking proteins and polypeptides to albumin or albumin derivatives are well known in the art. See, for example, U.S. Pat. No. 5,116,944.

D. Screening for Compounds that Modulate MK2 Activity

1. Use of the Yeast-2 Hybrid System for Drug Screening

The present invention also provides methods of screening for drugs that modulate MK2 activity, including but not limited to, antibodies, chemical agents, small molecules, proteins and peptides. In some embodiments, once a protein-protein interaction has been detected between MK2 and another protein by Y2H, the protein-protein interaction in Y2H can be used for high-throughput drug screening. For example, once a protein-protein interaction is detected, the positive yeast colonies (identified by color and growth, as described) harboring the two proteins such as MK2 and an interacting protein, can be treated with a drug including antibodies, chemical agents, peptides, proteins or small molecules. A change in color or growth of the positive yeast colonies in the presence of the drug would be indicative of an effect on the interaction between the two proteins.

In some embodiments, an MK2 interacting protein stimulates MK2 activity, which has a pro-inflammatory effect in a host including a cell, a tissue or a whole organism. Therefore, it would be desirable to identify drugs that would disrupt such an interaction. Accordingly, the Y2H system can be used to identify drugs that would disrupt the interaction between MK2 and a protein that stimulates MK2 activity, thereby leading to use of such drugs in the treatment or prevention of inflammation.

In other embodiments, an MK2 interacting protein inhibits MK2 activity, resulting in an anti-inflammatory effect in a host including a cell, a tissue or a whole organism. In such a case, the Y2H system can be used for identifying drugs that strengthen such an interaction, which may be monitored by changes in color and growth of yeast cells harboring the two proteins, as described herein. Such a drug can subsequently be used in the treatment or prevention of inflammation.

As discussed above, in case of certain conditions such as certain bacterial infections, it is desirable to have enhanced MK2 activity. Accordingly, the Y2H system can also be used for screening for drugs that strengthen the interaction between MK2 and an interacting protein, resulting in enhanced MK2 activity, and subsequently enhanced resistance to bacterial infection. Such drugs can be used for treatment or prevention of, for example, certain bacterial infections such as *Listeria monocytogenes* infection.

2. Use of an In Vitro Reconstitution System for Drug Screening

An in vitro reconstitution system can also be used for identification of drugs including but not limited to, small molecules, antibodies, peptides and chemical agents that modulate MK2 activity. For example, subsequent to the identification of a protein-protein interaction by any of the assays provided herein, the proteins can be treated in vitro with drugs that will inhibit interaction between the two proteins. As discussed above, it is desirable to identify drugs that would inhibit the interaction between MK2 and another protein, where such an interaction stimulates MK2 activity. In addition, an in vitro reconstitution system can be used for formation and isolation of protein complexes which include MK2 and at least one MK2 interacting protein. These complexes can subsequently be used for identification of compounds that inhibit or promote complex formation, thereby modulating inflammation and/or inhibit or stimulate activity of Mk2 in the complex, thereby modulating inflammation.

MK2 and an interacting protein are synthesized and $^{35}$S-labeled in an in vitro translation system such as the rabbit reticulocyte lysate-coupled transcription-translation system supplied by Promega (Madison, Wis.). Interaction between MK2 and the protein is confirmed by co-immunoprecipitation as described. Alternatively, recombinant MK2 and an interacting protein can be produced using an expression system such as *E. coli* or baculovirus insect cells. The interaction between these two proteins can then be detected by pull-down assays similar to co-immunoprecipitation, ELISA or fluorescence resonance energy transfer (FRET). A test compound is added to the mixture of in vitro translated proteins and co-immunoprecipitation is performed as described. A desirable compound is one that inhibits the interaction between MK2 and the protein, as determined by the lack of interaction or reduced interaction in an immunoprecipitation assay or a pull-down assay in case of recombinantly produced proteins. Such a compound can subsequently be used for the treatment or prevention of inflammation. Examples of compounds that can be tested for their effect on inflammation in assays of the invention include chemical agents, small molecules, peptides, proteins and antibodies.

An in vitro reconstitution system can also be used to identify compounds that bind MK2 and inhibit MK2 activity. For example, in vitro translated MK2 or purified MK2 can be incubated with a compound and subsequently tested for its ability to either phosphorylate a known substrate such as Hsp 27 or increase TNF-α biosynthesis, as described here. However, any assay can be used which measures MK2 activity. Thus, those compounds that inhibit MK2 activity are identified as drugs that can be used for inhibition or prevention of inflammation. Whereas, the compounds that increase MK2 activity can be used for treatment of certain conditions where an increase in MK2 activity is desired.

E. Pharmaceutical Compositions

The present invention provides compositions including proteins that bind MK2. Such compositions may be suitable for pharmaceutical use and administration to patients. The compositions typically contain one or more proteins that bind MK2 and a pharmaceutically acceptable excipient. The compositions also include protein complexes that contain MK2 and at least one MK2 interacting protein. As used herein, the phrase "pharmaceutically acceptable excipient" includes any and all solvents, dispersion media, coatings, antibacterial and antifungal agents, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions. The pharmaceutical compositions may also be included in a container, pack, or dispenser together with instructions for administration.

Pharmaceutical compositions of the invention also include compositions that comprise compounds including small molecules, antibodies, chemical agents, proteins and peptides that are identified by one or more methods described herein. Appropriate dosages for administration of these compounds for treatment or prevention of inflammation can easily be determined by a physician. Examples of dosages include, but are not limited to, 5 mg to 500 mg, 50 mg to 250 mg, 100 mg to 200 mg, 50 mg to 100 mg, 15 mg to 85 mg, 30 mg to 70 mg, and 40 mg to 60 mg.

A pharmaceutical composition of the invention is formulated to be compatible with its intended route of administration. Methods to accomplish the administration are known to those of ordinary skill in the art. The administration may, for example, be intravenous, intramuscular, rectal, or subcutaneous.

Solutions or suspensions used for subcutaneous application typically include one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetra acetic acid; buffers such as acetates, citrates or phosphates; and agents for the adjustment of tonicity such as sodium chloride or dextrose. The pH can be adjusted with acids or bases, such as hydrochloric acid or sodium hydroxide. Such preparations may be enclosed in ampoules, disposable syringes or multiple dose vials made of glass or plastic.

Pharmaceutical compositions suitable for injection include sterile aqueous solutions or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, one may include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

In some embodiments, proteins that bind MK2 are prepared with carriers that will protect the protein against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation (Mountain View, Calif.) and Nova Pharmaceuticals. Liposomal suspensions containing proteins that bind MK2 can also be used as pharmaceutically acceptable carriers. These can be prepared according to methods known to those skilled in the art, for example, as described in U.S. Pat. No. 4,522,811.

Additional therapeutically useful agents beneficial for the condition being treated may optionally be included in or administered simultaneously or sequentially with proteins that bind MK2.

It is especially advantageous to formulate compositions in dosage unit form for ease of administration and uniformity of dosage. Dosage unit form as used herein refers to physically discrete units suited as unitary dosages for the subject to be treated. Each unit typically contains a predetermined quantity of active compound calculated to produce the desired therapeutic effect in association with the required pharmaceutical carrier. The specification for the dosage unit forms of the invention are dictated by and directly dependent on the unique characteristics of an active compound and the particular therapeutic effect to be achieved, and the limitations inherent in the art of using such an active compound for the treatment of individuals.

F. Treatment Indications

Compounds that interact with at least one of MK2 or an MK2 complex are useful to prevent, diagnose, or treat various medical conditions in humans or animals. Accordingly, the present invention provides a method for treating conditions related to inflammation, by administering to a subject a composition comprising at least one compound (such as a protein, peptide, antibody, chemical agent, and small molecule) that interacts with at least one of MK2 or an MK2 complex in an amount sufficient to ameliorate the symptoms of the condition. Such conditions include Crohn's disease, inflammatory bowel disease, ulcerative colitis, rheumatoid arthritis, acute respiratory distress syndrome, emphysema, delayed type hypersensitivity reaction, asthma, systemic lupus erythematosus, and inflammation due to trauma or injury or stroke.

G. Methods of Treatment Using Compounds that Interact with MK2 or an MK2 Complex Compounds that interact with MK2 or an MK2 complex, and modulate MK2 activity may be used to inhibit or reduce one or more symptoms associated with inflammation. In an embodiment, inflammation is inhibited at least 50%, or at least 60, 62, 64, 66, 68, 70, 72, 72, 76, 78, 80, 82, 84, 86, or 88%, or at least 90, 91, 92, 93, or 94%, or at least 95% to 100%. Compounds may be used individually or in combination.

Pharmaceutical preparations comprising compounds, as described herein, are administered in therapeutically effective amounts. A compound that modulates MK2 activity can be selected from a protein, a peptide, an antibody, a chemical agent or a small molecule. As used herein, an "effective amount" of the compound is a dosage that is sufficient to reduce inflammation to achieve a desired biological outcome. Such improvements may be measured by a variety of methods including those that measure symptoms such as pain, swelling, or redness. For example, an American College of Rheumatology (ACR) score is used to measure inflammation in rheumatoid arthritis. An ACR score is defined as $\geq$20%, 50%, or 70% improvement in tender joint and swollen joint count plus $\geq$20%, 50%, or 70% improvement in at least 3 of the following 5 criteria: patient pain assessment, physician and patient global assessments, patient self-assessed disability, and acute phase reactant (erythrocyte sedimentation rate and C-reactive protein level). However, it is understood that a physician will be able to diagnose and measure inflammation in any disorder and determine whether a decrease in inflammation is achieved using an anti-inflammatory drug identified using methods of the invention.

Generally, a therapeutically effective amount may vary with the subject's age, condition, and sex, as well as the severity of the medical condition in the subject. The dosage may be determined by a physician and adjusted, as necessary, to suit observed effects of the treatment. Appropriate dosages for administering at least one compound that interacts with MK2 or an MK2 complex, and modulates MK2 activity, may range from 5 mg to 500 mg, 50 mg to 250 mg, 100 mg to 200 mg, 50 mg to 100 mg, 15 mg to 85 mg, 30 mg to 70 mg, and 40 mg to 60 mg. These compounds can be administered in one dose, or at intervals such as once daily, once weekly, and once monthly. Dosage schedules can be adjusted depending on the ability of the protein to decrease inflammation, the half-life of the protein, or the severity of the patient's condition. Generally, the compositions are administered as a bolus dose, to maximize the circulating levels of these compounds for the greatest length of time after the dose. Continuous infusion may also be used after the bolus dose.

Toxicity and therapeutic efficacy of such proteins or compounds can be determined by standard pharmaceutical procedures. Experiments could be performed in cell culture to determine an effect of the proteins or compounds on cytokine expression or activity. Experiments could also be performed in experimental animals, e.g., for determining the $LD_{50}$ (the dose lethal to 50% of the population) and the $ED_{50}$ (the dose therapeutically effective in 50% of the population). The dose ratio between toxic and therapeutic effects of a compound is its therapeutic index, which can be expressed as $LD_{50}/ED_{50}$. Compounds that interact with MK2 or an MK2 complex, and modulate MK2 activity, including but not limited to, peptides, proteins, antibodies, chemical agents and small molecules, and which exhibit large therapeutic indices may be used in methods of treatment of the invention.

Data obtained from cell culture assays and animal studies can be used in evaluating a range of dosage for use in humans. A dosage of such proteins and compounds may lie within a range of circulating concentrations that include the $ED_{50}$ value with little or no toxicity. The dosage may vary within this range depending upon the dosage form employed and the route of administration utilized. For any compound that interacts with MK2 or an MK2 complex, the therapeutically effective dose can be estimated initially from cell culture assays as described. A dose may be formulated in animal models to achieve a circulating plasma concentration range that includes the $IC_{50}$ value (i.e., the concentration of the test protein which achieves a half-maximal inhibition of symptoms) as determined in cell culture. Levels in plasma may be measured, for example, by high performance liquid chromatography. Effects of any particular dosage can be monitored by a suitable bioassay.

H. Methods of Treatment Using Cells

Another way to administer proteins, peptides, or antibodies that interact with MK2 or an MK2 complex, and modulate MK2 activity, to a host is to administer cells that express these compounds. Various methods can be used to deliver cells expressing proteins, peptides or antibodies to a site for use in modulating inflammation. In one embodiment of the invention, cells expressing a protein, peptide or antibody can be administered by targeted delivery, for example, direct injection of a sample of such cells into a specific site in a tissue that has inflammation. The cells can be delivered in a medium or matrix that partially impedes their mobility so as to localize the cells to a site of interest. Such a medium or matrix could be semi-solid, such as a paste or gel, including a gel-like polymer. Alternatively, the medium or matrix could be in the form of a solid, a porous solid which will allow the migration of cells into the solid matrix, and hold them there while allowing proliferation of the cells. In some embodiments, a host cell includes a first nucleic acid encoding a recombinant MK2 polypeptide and a second nucleic acid encoding an MK2 interacting protein such as, for example, STS, HPH2 and Shc. An MK2 complex containing MK2 and at least one other protein can subsequently be isolated from the host cell.

I. Methods of Expressing DNA in a Cell

DNA encoding proteins, peptides, and antibodies that interact with MK2 or an MK2 complex, and modulate MK2 activity, can be introduced into a cell. Proteins, peptides and antibodies encoded by the DNA can then be expressed in such a cell. In some embodiments of the invention, a DNA molecule encoding a protein, peptide, or antibody that interacts with MK2 or an MK2 complex, thereby modulating MK2 activity, could be introduced into a cell in order to alter the production or activity of cytokines in the cell. Specifically, a DNA molecule encoding a protein, peptide or antibody could be introduced into a cell to reduce or inhibit the production or activity of cytokines.

Delivery of polynucleotide sequences of proteins, peptides or antibodies can be achieved using a recombinant expression vector such as a chimeric virus or a colloidal dispersion system. Target liposomes may be used for therapeutic delivery of the polynucleotide sequences. Various viral vectors that can be utilized for introducing DNA into cells include adenovirus, herpes virus, vaccinia, or an RNA virus such as a retrovirus. A retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous sarcoma virus (RSV). A number of additional retroviral vectors can incorporate multiple genes, for example, vectors that can encode polycistronic messages or those that include multiple promoters. All of these vectors can transfer or incorporate a gene for a selectable marker so that transduced cells can be identified and generated.

Since recombinant retroviruses are defective, they require helper cell lines that contain plasmids encoding all of the structural genes of a retrovirus under the control of regulatory sequences within the long terminal repeat sequences of viruses. These plasmids are missing a nucleotide sequence that enables the packaging mechanism to recognize an RNA transcript for encapsidation. Helper cell lines that have deletions of the packaging signal include, but are not limited to, for example, PSI.2, PA317 and PA12. These cell lines produce empty virions, since no genome is packaged. If a retroviral vector is introduced into cells in which the packaging signal is intact, but the structural genes are replaced by other genes of interest, the vector can be packaged and vector virion produced.

Alternatively, a second type of cell in tissue culture can be directly transfected with a plasmid encoding the retroviral structural genes gag, pol and env, by conventional calcium phosphate transfection. These cells are then transfected with a vector plasmid containing the genes of interest. The resulting cells release the retroviral vector into the culture medium, and the vectors are subsequently introduced into appropriate cells.

Another targeted delivery system for a polynucleotide encoding a protein, peptide or antibody is a colloidal dispersion system. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles that are useful as delivery vehicles. RNA, DNA and intact virions can be encapsulated within the aqueous interior and be delivered to cells in a biologically active form (see, for example, Fraley et al., Trends Biochem. Sci., 6: 77 (1981)). Methods for efficient gene transfer into a cell using a liposome vehicle are known in the art (see, for example, Mannino et al., Biotechniques, 6: 682 (1988). The composition of liposome usually includes a combination of phospholipids, typically in combination with steroids, especially cholesterol. Other phospholipids or lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine and distearoylphosphatidylcholine.

J. Methods of Expressing DNA in a Tissue, Organ, or Organism

DNA encoding proteins that bind MK2, including antibodies, and DNA encoding proteins, peptides and antibodies that modulate MK2 activity by binding an MK2 complex can be introduced into a cell within a tissue, an organ, or an organism. Proteins, peptides or antibodies encoded by the DNA can then be expressed in the cell of the tissue, organ, or organism. In one embodiment of the invention, DNA encoding proteins, peptides or antibodies could be introduced to a cell in order to alter the production or activity of cytokines in the cells of the tissue, organ, or organism. This method could be used to decrease inflammation in tissues, organ, or organism. The invention is useful for treating conditions such as Crohn's disease, inflammatory bowel disease, ulcerative colitis, rheumatoid arthritis, acute respiratory distress syndrome, emphysema, delayed type hypersensitivity reaction, asthma, systemic lupus erythematosus, and inflammation due to trauma or injury.

In one embodiment of the invention, DNA encoding proteins, peptides, or antibodies that interact with MK2 or an MK2 complex, and modulate MK2 activity, can be targeted to a specific cell type of interest. The cell type can be a component of a tissue, organ, or organism. By inserting a sequence of interest into the viral vector, along with another gene which encodes the ligand for a receptor on a specific target cell, for example, the vector is now specific for a certain cell type, and thus may be specific for a certain tissue, organ, or organism. Retroviral vectors can be made target specific by attaching, for example, a sugar, a glycolipid, or a protein. Targeting may be accomplished by using an antibody. Those of skill in the art will recognize that specific polynucleotide sequences can be inserted into the retroviral genome or attached to a viral envelope to allow target specific delivery of the retroviral vector containing the polynucleotide of proteins, peptides or antibodies. The targeting of liposomes is also possible based on cell specificity as known in the art.

In another embodiment of the invention, cells can be removed from a tissue, organ, or organism, DNA encoding a protein, peptide or antibody that interacts with MK2 or an MK2 complex, and modulates MK2 activity, can be introduced into the cells, and the cells can be reintroduced into the tissue, organ, or organism. These cells would then produce the protein, peptide, or antibody when delivered into a tissue, organ, or organism of interest. Cells can be reintroduced to the tissue, organ, or organism by the methods described above.

K. Methods of Detection and Isolation of MK2

Compounds that interact with at least one of MK2 or an MK2 complex may be used to detect the presence or amount of MK2, in vivo or in vitro. These include proteins, peptides, antibodies, chemical agents, and small molecules. By correlating the presence or level of MK2 interacting proteins with a medical condition, one of skill in the art can diagnose the associated medical condition. The medical conditions that may be diagnosed by these compounds are set forth herein.

Such detection methods are well known in the art and include ELISA, radioimmunoassay, immunoblot, Western blot, immunofluorescence, immunoprecipitation, and other comparable techniques. These compounds may further be provided in a diagnostic kit that incorporates one or more of these techniques to detect MK2. Such a kit may contain other components, packaging, instructions, or other materials to aid detection of MK2 and uses of the kit.

Where compounds that interact with MK2 or an MK2 complex, and modulate MK2 activity, are intended for diagnostic purposes, it may be desirable to modify them, for example with a ligand group (such as biotin) or a detectable marker group (such as a fluorescent group, a radioisotope or an enzyme). If desired, they may be labeled using conventional techniques. Suitable labels include fluorophores, chromophores, radioactive atoms, electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. Other suitable binding partners include biotin and avidin or streptavidin, IgG and protein A, and the numerous receptor-ligand couples known in the art. Other permutations and possibilities will be readily apparent to those of ordinary skill in the art, and are considered as equivalents within the scope of the instant invention.

Compounds that interact with at least one of MK2 or an MK2 complex may also be useful for isolating MK2 in a purification process. In one type of process, compounds may be immobilized, for example, through incorporation into a column or resin. The compounds are used to bind MK2, and then subjected to conditions which result in the release of the bound MK2. Such processes may be used for the commercial production of MK2.

The following examples provide various embodiments of the invention. One of ordinary skill in the art will recognize the numerous modifications and variations that may be performed without altering the spirit or scope of the present invention. Such modifications and variations are believed to be encompassed within the scope of the invention. The examples do not in any way limit the invention. It is understood that all of the numbers in the specification and claims are modified by the term about, as small changes in dosages, for example, would be considered to be within the scope of the invention.

EXAMPLES

Example 1

Preparation of the cDNA Library

Methods for performing the yeast two-hybrid screening were adapted from the Pretransformed Matchmaker Libraries User Manual published by Clontech (Palo Alto, Calif., USA; versions PT3183-1; PR1X299).

A pretransformed human bone marrow cDNA library was purchased from Clontech (# HY4053AH). This cDNA library was pretransformed into *Saccharomyces cerevisiae* host strain Y187 (Clontech). The yeast cells were kept frozen before use.

DNA-bait construct in a yeast reporter strain AH109 (Clontech) served as a mating partner for the Y187 yeast.

Example 2

Preparation of the MK2-Bait Construct

To prepare the MK2 construct comprising a binding domain (BD), an MK2 gene fragment encoding the full length kinase in which amino acid lysine 93, in the ATP binding pocket had been mutated to an arginine was generated by directional cloning into the DNA-BD vector, pGBKT7 (Clontech) to generate MK K93R-pGBKT7. The lysine at position 93 was converted to an arginine to produce a catalytically inactive form of the kinase. Specifically, the pGBKT7 vector was digested with Nde-Xho, and purified using agarose gel electrophoresis. The MK2 fragment was ligated into the pGBKT7 vector by using T4 DNA ligase. Plasmids containing the inserts were identified by restriction analysis. Yeast were transformed with the MK2 construct and MK2 expression was subsequently confirmed in the transformed AH109 yeast strain.

Toxicity of the protein encoded by the MK2 construct on the host cell was investigated by comparing the growth rate of cells transformed with the MK2 construct and cells transformed with the empty vector. The MK2 construct was determined to be not toxic. Cells with the bait construct or with the empty vector grew at substantially the same rate and cell number.

To analyze transcriptional activation, cells transformed with the MK2 construct were plated on SD/-Trp/X-α-Gal (Clontech), SD/-His/-Trp/X-α-Gal (Clontech), and SD/-Ade/-Trp/X-α-Gal media (Clontech). Results showed that the MK2 protein by itself does not activate transcription. The yeast containing the MK2 bait construct produced tryptophan, however, these yeast did not produce Adenine or Histidine. Clones grew on the SD/-Trp/X-α-Gal medium, but did not appear blue. Clones did not grow on SD/-His/-Trp/X-α-Gal or SD/-Ade/-Trp/X-α-Gal media, showing that there was no general transcriptional activation of endogenous reporter genes.

Example 3

Screening the Yeast Two-Hybrid Library

The MK2 used in the screening the library was full length and catalytically inactive. This inactive mutant encodes an alanine substitution at the conserved lysine in the MK2 ATP binding pocket rendering MK2 inactive (Kotlyarov et al., Mol Cell Bio 22, 4827-4835 (2002)) form was used because inactive kinases are known to bind interacting proteins more stably thereby allowing for stronger transcriptional activation of 2 hybrid reporter genes.

A colony of yeast transformed with the MK2 construct was inoculated in SD/-Trp (Clontech) medium at 30° C. overnight with shaking at 250-270 rpm. The next day, the $OD_{600}$ was measured to be >0.8. The cells were spun down by centrifugation at 1000×g for 5 minutes. The supernatant was decanted and the cell pellet was resuspended in residual liquid by vortexing.

One frozen aliquot (~1.0 ml) of the library culture was thawed in a room temperature water bath. The cells were gently vortexed. The entire MK2 bait culture and the 1 ml library culture were combined. 45 ml of 2×YPDA/Kan (a blend of yeast extract, peptone, dextrose, adenine, and kanomycin; Clontech) was added to the culture and swirled gently, and the volume was brought to 50 ml with 2×YPDA/Kan. The cells were incubated overnight at 30° C. with gentle swirling (30-50 rpm).

Cells were transferred to a sterile centrifuge bottle and spun down by centrifugation at 1000×g for 10 minutes. The pellet was resuspended in 50 ml 2×YPDA/Kan, then the cells were spun down at 1000×g for 10 minutes. This wash step was repeated. Subsequently cells were resuspended in 10 ml of 0.5×YPDA/Kan medium.

Two hundred μl of the mating mixture was plated on approximately 50 large (150 mm) SD/-His/-Leu/-Trp plates (Clontech). The plates were incubated, colony side down, at 30° C. until colonies appeared on the plates. Clones were scored for growth on SD/-Leu (Clontech), SD/-Trp, and SD/-Leu/-Trp (Clontech) plates. Haploid and diploid cells grew on the SD/-Leu or SD/-Trp media. Only diploid cells grew on the SD/-Leu/-Trp medium. Mating efficiency was determined to be 5.4%.

Colonies growing on plates containing SD/-His/-Leu/-Trp X-α-Gal medium were restreaked onto SD/-His/-Leu/-Trp X-α-Gal plates to verify the phenotype. Next, the clones were screened on the more stringent SD/-Ade/-His/-Leu/-Trp plates containing X-α-GAL (Clontech). Positive colonies were restreaked onto SD/-Ade/-His/-Leu/-Trp in a grid fashion (Clontech) to generate master plates. DNA preps and glycerol stocks of the yeast were made from these master plates.

Example 4

Analysis of Putative Positive Clones

The YEASTMAKER™ Yeast Plasmid Isolation Kit (Clontech; #K1611-1) provided the reagents and tools for isolating plasmid from yeast. Yeast were obtained from individual positives which had been streaked onto the master plates, and were resuspended in 50 μl Tris EDTA in a 96 well format. Ten μl lyticase was added to each well. The plate was incubated at 37° C. for 1 hour after which 20 μl of 20% SDS was added. The DNA was purified using a Qiagen turbo prep (Qiagen, Valencia, Calif., USA). Samples were PCR amplified using an Advantage 2 PCR enzyme (Clontech; # K1910-1). Inserts were identified by sequencing.

Example 5

Analysis of Positive Clones

Independent sequences were transformed into bacteria (DH5 α) from which DNA was subsequently isolated. Next, the DNA was transformed into yeast strain AH109. Several bates: MK2, catalytically inactive MK2 K93R, empty vector pGBKT7, TPL2, p53, and Lamin (Clontech) were transformed into yeast strain Y187. Each independent sequence strain transformed in AH109 was mated with Y187 yeast transformed with each of the three baits. Independent clones which interacted with MK2 and MK2 K93R, but not with empty vector pGBKT7, TPL2, p53, or Lamin, as assayed by their growth on SD/-Ade/-His/-Leu/-Trp and blue color on SD/-Leu/-Trp X-α-GAL, were identified as clones which included DNA inserts encoding specific MK2 interacting proteins (FIG. 9A). MK2 interacting proteins bound wild type MK2 and MK2 K93R with substantially the same affinity, illustrating that MK2 binding is not an artifact of the kinase inactive mutant MK2 K93R. One protein encoded by an independent DNA sequence characterized was "similar to smoothelin" (STS). The cDNA sequence encoding the protein is provided in FIG. 1 and SEQ ID NO: 1; the amino acid sequence is provided in FIG. 4 and SEQ ID NO: 4.

Another protein encoded by an independent clone was human polyhomeotic2 (HPH2). The cDNA sequence encoding the protein is provided in FIG. 2 and SEQ ID NO: 2; the amino acid sequence is provided in FIG. 5 and SEQ ID NO: 5. HPH2 has a sterile alpha motif (SAM) protein interaction domain.

Yet another protein encoded by an independent DNA sequence isolated was src homology and collagen (Shc). The cDNA sequence encoding the protein is provided in FIG. 3 and SEQ ID NO: 3; the amino acid sequence is provided in FIG. 6 and SEQ ID NO: 6. The longest isoform of Shc (p66 Shc A) has an N terminal CH2 domain followed by a PTB, CH1, and an SH2 domain at the C terminus of the protein.

Example 6

Delineation of MK2 Interaction Domains

To delineate the MK2 domain required for interaction with Shc A, HPH2, and STS several, MK2 deletion mutants were used. MK2 mutants tested included MK2∇N (MK2 amino acids 41-400), MK2∇C (MK2 amino acids 1-370) as well as MK2Cat (MK2 catalytic domain amino acids 41-338). MK2∇N has the proline rich N-terminus deleted, MK2∇C has the MK2 nuclear localization signal (NLS) and the p38 binding site deleted, and MK2Cat has the N terminal proline rich domain as well as the C terminal auto-inhibitory domain, nuclear export signal (NES) and NLS deleted. 2-hybrid analysis showed that Shc A interacts equally well with full length MK2, MK2∇C, and MK2Cat. Interaction with MK2∇N, however, was barely detectable. The interaction profile with Shc A indicates that minimally, Shc A interacts with the MK2 catalytic domain and that deleting the MK2 N-terminus might induce a conformational change such that Shc A no longer binds MK2 efficiently.

HPH2 binds full length MK2, MK2∇N and MK2∇C with substantially the same affinity. Interaction with MK2Cat, however, was less pronounced. HPH2, therefore, seems to require binding at the MK2 N- or C-terminus while the MK2 catalytic domain when expressed alone does not promote HPH2 binding with MK2 to a comparable level.

Similar to smoothelin binds MK2 with higher affinity than either Shc A or HPH2 as assayed by growth and color assays in yeast. Additionally, similar to smoothelin binds each of MK2, MK2∇N, MK2∇C and MK2Cat with substantially the same affinity indicating that multiple sites in MK2 interact with this protein.

Example 7

MK2 Co-Immunoprecipitates with Shc A and HPH2 in Mammalian Cells

Figure 10A:
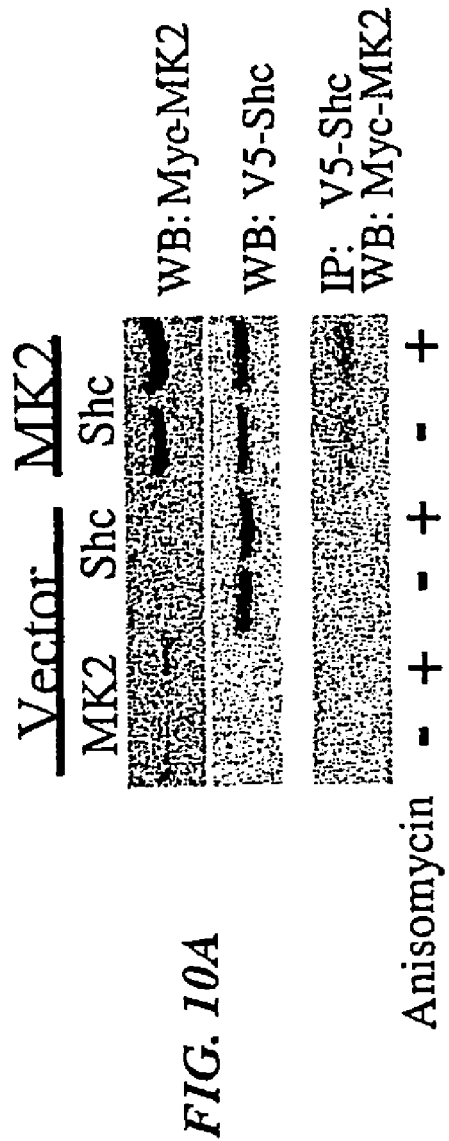
As shown in FIG. 10A, Western blotting using antibodies against V5 or Myc shows that both V5-tagged Shc and Myc-tagged MK2 proteins are expressed in 293T cells. Co-immunoprecipitation using the anti-V5 antibody and subsequent immunoblotting with the anti-Myc antibody shows that MK2 co-immunoprecipitates with Shc.

V5-tagged Shc and MYC-tagged MK2 were co-expressed in 293T cells, as shown in FIG. 10A. Cells were unstimulated or stimulated with 10 μg/ml anisomycin for 30 minutes. Western blotting of cell lysates using antibodies against V5 or Myc show that both V5-tagged Shc and MYC-tagged MK2 proteins were expressed. Cell lysates were immunoprecipitated with the anti-V5 antibody. Immunoprecipitates were resolved by SDS PAGE and immunoblotted with anti-MYC antibody. The anti-MYC antibody binds to the immunoblot, indicating that MYC-tagged MK2 co-immunoprecipitated with V5-tagged Shc. This indicates an interaction between MK2 and Shc.

Figure 10B:
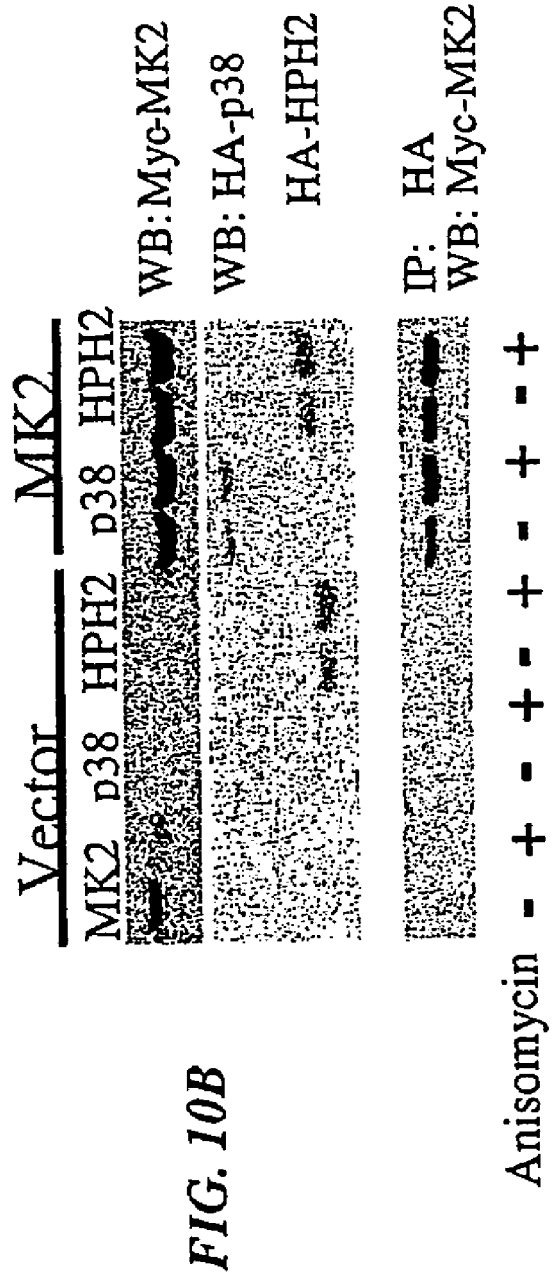
FIG. 10B shows that HA-HPH2, HA-p38, and Myc-MK2 were expressed, as detected by Western blotting. Co-immunoprecipitation using the anti-HA antibody and subsequent immunoblotting with the anti-Myc antibody shows that MK2 co-immunoprecipitates with HPH2 and p38.

In a similar experiment, co-immunoprecipitation using the anti-HA antibody and subsequent immunoblotting with the anti-Myc antibody shows that MK2 co-immunoprecipitates with HPH2 and p38 (FIG. 10B). HA-tagged p38, HA-tagged HPH2, and Myc-tagged MK2 were expressed in 293T cells, as shown by Western blotting.

Co-immunoprecipitation can be used to detect the binding of two proteins or to confirm results of binding between two proteins as found in other methods, such as the Y2H system.

Example 8

Effect of Binding Proteins on MK2 Activation

An HA-tagged MK2 interacting protein (for example, Shc), and MYC-tagged MK2 are co-expressed in 293T cells. Cell lysates are prepared and resolved by SDS PAGE. Subsequent immunoblotting with Myc and HA antibodies to detect MYC-tagged MK2 and the HA-interacting protein will confirm that these proteins are expressed. Since activation of MK2 comprises phosphorylation of MK2, immunoblotting with an antibody to detect phosphorylated MK2 (for example, anti-phospho MK2 threonine 334 (p334)), will determine the activation state of MK2. A difference in the amount of MK2 344 when co-expressed with an MK2 activator, compared to the amount of MK2 p334 when MK2 is expressed alone, will indicate altered activity of MK2 in the presence of the MK2 interacting protein.

Example 9

Effect of MK2 Interacting Proteins on TNF Biosynthesis

Figure 11:
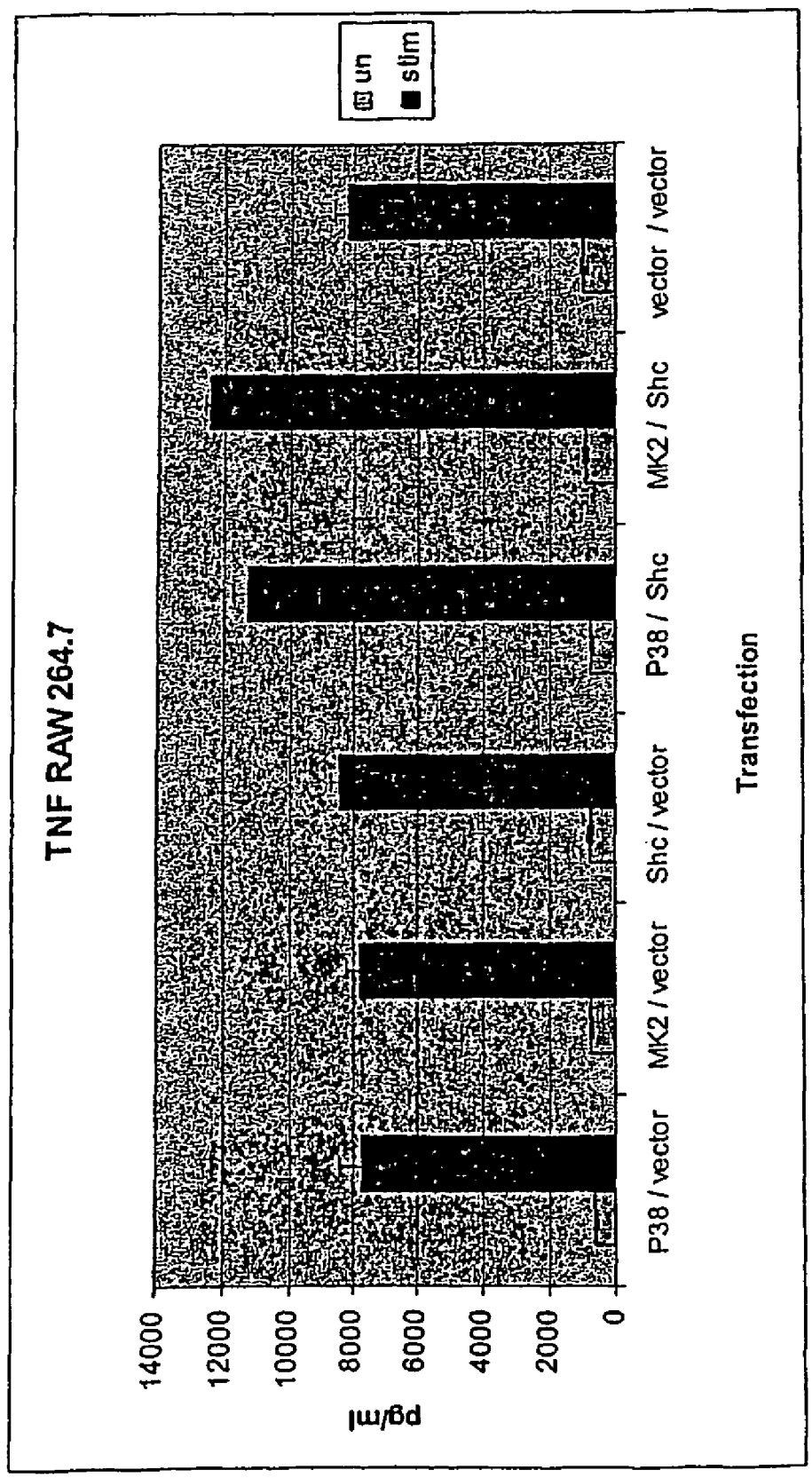
FIG. 11 depicts levels of TNF-α protein (pg/ml) in RAW264.7 macrophage cells. As shown, TNF-α levels are increased in anisomycin stimulated RAW264.7 macrophage cells co-expressing either p38 and Shc or MK2 and Shc compared to TNF-α levels in cells containing vector alone, p38 alone, MK2 alone or Shc alone. Thus, Shc appears to be pro-inflammatory as it enhances MK2 activity.

Two empty vector constructs were co-expressed in RAW 264.7 macrophage cells to establish a basal level of TNF-α biosynthesis, as detected by ELISA (FIG. 11). Cells were either unstimulated or stimulated with lipopolysaccharide (LPS) to stimulate MK2 catalytic activity. The level TNF expression-α was detected in cells in which MK2, p38, or Shc was co-expressed with empty vector and levels were comparable to the basal level found with vector alone. When cells co-expressed p38 and Shc, the level of TNF-α expression was greater than that detected in controls. Similarly, co-expression of Shc and MK2 resulted in an increase in TNF-α levels.

Example 10

Effect of MK2 on the Phosphorylation State of an MK2 Interacting Protein

An HA-tagged MK2 interacting protein is expressed in 293T cells. Cell lysates are prepared and immunoprecipitated with an anti-HA antibody. The immunoprecipitates are used in an in vitro kinase assay with recombinant MK2 added as kinase. SDS PAGE followed by phosphoimagery is used to detect phosphorylation of the MK2 interacting protein. Phosphorylation of the MK2 binding or interacting protein in the presence of MK2 and reduced or no phosphorylation of the MK2 interacting protein in the absence of MK2 would indicate that MK2 phosphorylates the MK2 interacting protein. An MK2 interacting protein may or may not be a substrate for MK2.

Example 11

Detection of MK2 Interacting Proteins Using a Proteomics Approach

A proteomics approach can be used to identify MK2 interacting proteins. Wild type (+/+) or MK2 deficient (−/−) cells were plated and labeled with $^{33}$P. MK2 was activated for 30 minutes following which whole cell lysates were prepared and analyzed using two dimensional gel electrophoresis. Gels were compared to identify differentially phosphorylated proteins. FIG. 12A shows a differentially phosphorylated protein (arrow) with an isoelectric focusing point of 5.4. The absence of phosphorylation in MK2+/+ cells may be due to phosphorylation dependent changes in protein migration. FIG. 12B shows a silver stain of the same region showing abundance of proteins resolved.

Example 12

MK2 is Activated when Co-Expressed with Shc A in HeLa Cells

The activation state of MK2 when co-expressed with Shc A was determined. Hsp 27 is a physiological substrate for MK2. Phosphorylation of endogenous HSP 27 in HeLa cells is responsive to MK2 and therefore, can be used to determine MK2 activity. HeLa cells were transfected either with vector alone, or with vector and V5-Shc A or Myc-MK2 as controls. In parallel, cells were co-transfected with both V5-Shc A and Myc-MK2. After allowing for expression, cells were left either unstimulated or stimulated for 30 minutes with anisomycin to activate MK2. Subsequent immunoblotting with an anti-phospho peptide specific antibody against phosphorylated Hsp 27 (pHsp 27) shows an increase in pHsp 27 upon stimulation. With expression of exogenous Myc-MK2 there was an increase in basal pHsp 27 levels in unstimulated cells (FIG. 13A). This increase in basal phosphorylation is not observed in Shc A or vector control expressing cells. Quantitation of these results using densitometry shows that the increase in basal pHsp 27 seen with Myc-MK2 expression as compared with empty vector or V5-Shc A is 1.5-2 fold. Basal pHsp 27 levels were further increased when Myc-MK2 was co-expressed with V5-Shc A. Quantitation shows this increase to be 3 fold over levels detected when Myc-MK2 was expressed alone (FIG. 13B). As shown in 293T cells, MK2 levels increased with co-expression of Shc A, further illustrating the interaction between MK2 and Shc A. The observed increase in basal pHsp 27 is likely to reflect increased MK2 activity as well as increased levels of MK2 protein. Basal pHsp 27 was shown to increase 2 to 3 fold when normalized with MK2 levels (FIG. 13C). This increase is proposed to reflect the activation of MK2 with co-expression of Shc A.

Increased MK2 activity is observed with co-expression of p66 Shc A. Phosphorylation of endogenous Hsp 27 is responsive to MK2 activity in HeLa cells. Increased pHsp 27 is observed with MK2-p66 Shc A co-expression indicating that MK2 is activated with p66 Shc A binding. The observed increase in TNF-α levels with MK2-p66 Shc A co-expression in RAW 264.7 cells confirms that MK2 is activated with Shc A co-expression. MK2 activation with p66 Shc A may result in MK2 localization and retention in the cytosol through Shc A binding. Cytosolic localization may in turn increase MK2's access to cytoplasmic substrates such as Hsp 27 and TNF-α mRNA. Alternatively, MK2 may bind cytosolic Shc promoting MK2 cytoplasmic localization where it becomes further activated.

Example 13

MK2 is Activated when Co-Expressed with Shc A in RAW264.7 Cells

Figure 14A:
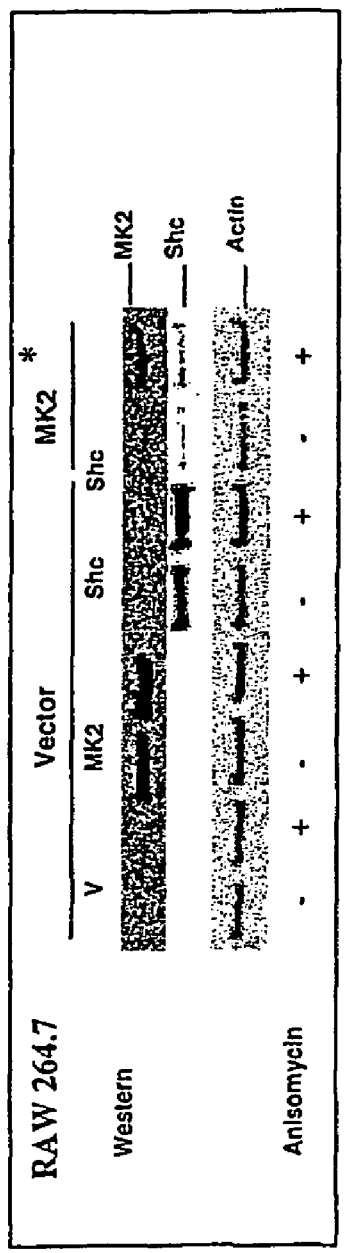
FIG. 14A depicts a western blot showing that Shc and MK2 are expressed in RAW264.7 cells. An anti-actin antibody is used to show that equal amounts of total protein were loaded in each lane.

MK2 was activated when co-expressed with Shc A, as assayed by levels of pHsp 27 in HeLa cells. To further confirm that MK2 is activated upon association with Shc A, secreted TNF protein from RAW264.7 cells was assayed for in presence of both MK2 and Shc A. Data from cells derived from mice deleted for MK2 show a 90% decrease in TNF-α biosynthesis in response to LPS. Subsequent experiments have shown that catalytically active MK2 is required to restore TNF biosynthesis in these cells, thereby establishing MK2 enzymatic activity as necessary for TNF-α biosynthesis. RAW264.7 cells were transfected with either vector alone, or were co-transfected with vector and V5-Shc A or Myc-MK2 as controls. In parallel, cells were co-transfected with both V5-Shc A and Myc-MK2. After allowing for expression, cells were left either unstimulated or stimulated with LPS for 30 minutes to activate MK2. Quantitative western blot analysis shows that both Myc-MK2 and V5-Shc A are expressed in RAW264.7 cells. In contrast to co-expression in 293T and HeLa cells, levels of both MK2 and Shc A decreased when co-expressed in RAW264.7 cells. This decrease does not reflect an overall decrease in protein levels because equal amounts of protein were loaded in each lane as shown using an actin specific antibody (FIG. 14A).

Figure 14B:
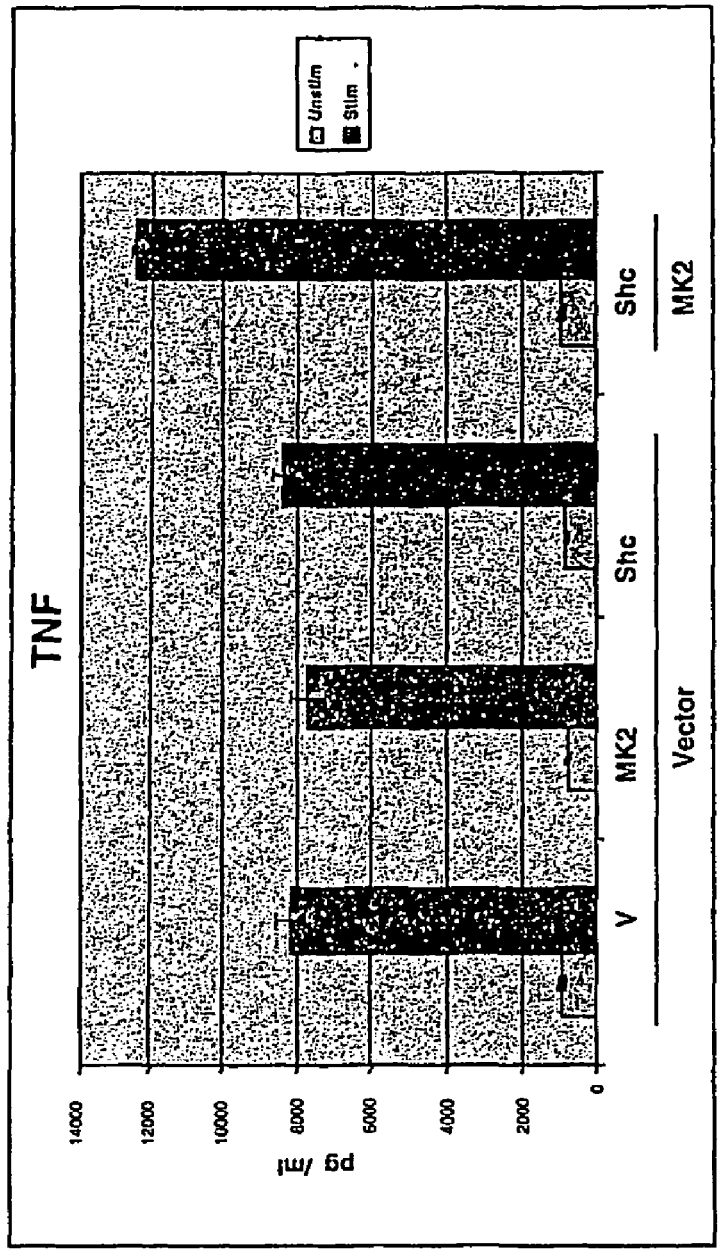
FIG. 14B depicts the levels of secreted TNF-α protein, as measured by ELISA, in both LPS-stimulated and unstimulated. RAW264.7 cells transfected with vector alone (V), MK2 alone, Shc alone or MK2 and Shc.

TNF ELISAs showed that TNF-α secretion increased 8 fold upon stimulation by LPS and that expression of Myc-MK2 or V5-Shc A alone does not potentiate TNF biosynthesis in these cells. In contrast, when MK2 and Shc A were co-expressed TNF-α biosynthesis increases 1.5 fold after stimulation. (FIG. 14B). The increase in TNF biosynthesis is proposed to reflect an increase in MK2 activity and not in MK2 expression since MK2 protein levels when co-expressed with Shc A, are below those observed in cells expressing MK2 alone.

Example 14

MK2 Phosphorylates Shc A In Vitro

Figure 15A:
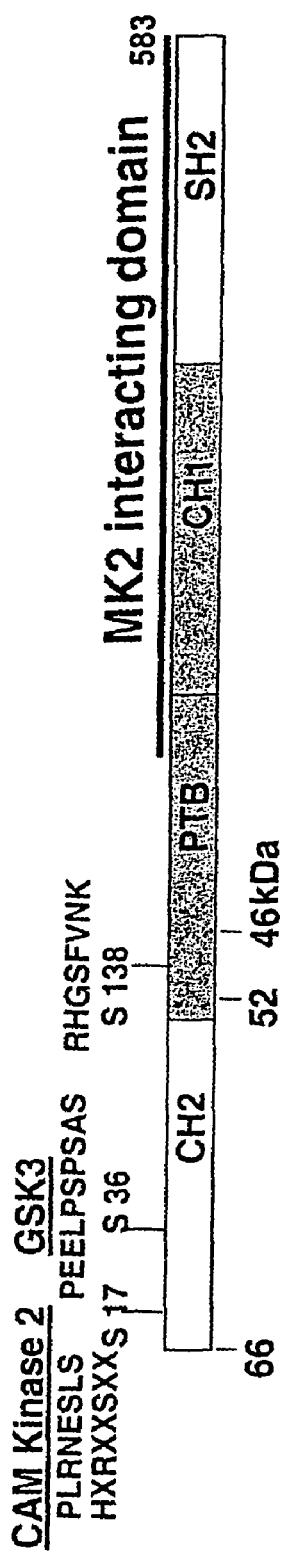
FIG. 15A depicts a schematic representation of the p66Shc A protein including a CH2 domain, a PTB domain, a CH1 domain and a SH2 domain. Also shown is the MK2 interacting domain in the protein, the CAM kinase 2 consensus sequence and GSK3 sequence.

P66 Shc is phosphorylated at serine 36 within the CH2 domain upon oxidative stress. N-terminal to S36, a serine is located at position 17 (S17) within a Cam kinase II consensus sequence: RXXS. FIG. 15A depicts a schematic representation of the Shc A protein, including various phosphorylation sites within the protein. The RXXS motif has been shown to serve as a substrate for MK2 although it does not contain a hydrophobic amino acid often found −2 from the conserved Arginine in the MK2 consensus motif. To determine if Shc A is a substrate for MK2, V5-Shc A was expressed in 293T cells. After expression, Shc A was immunoprecipitated using an anti-V5 antibody. Immunoprecipitates were subsequently used in an in vitro kinase assay with exogenously added activated recombinant MK2. Vector transfected control cells showed low levels of phosphorylation at 66-kDa most likely resulting from the anti-V5 antibody immunoprecipitating a protein endogenous to 293T cells which serves as a weak substrate for MK2. Only Shc A transfected cells showed robust phosphorylation at 66-kDa demonstrating that Shc A is a substrate for MK2 in vitro. Coomassie staining and immunoblotting using an anti-V5 antibody showed that Shc A was expressed in Shc A transfected cells. (FIG. 16B)

Figure 15B:
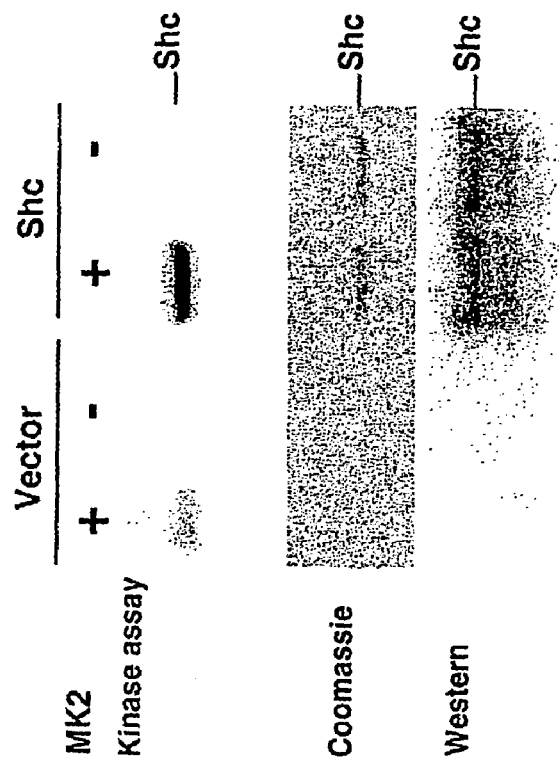
FIG. 15B depicts phosphorylation of p66Shc A in an in vitro kinase assay using recombinant MK2 and V5-Shc A immunoprecipitated from transfected 293T cells. As depicted, phosphorylated Shc A is detected only in immunoprecipitates from cells expressing Shc. Coomassie staining and western blotting using an anti V5-antibody are used to confirm that Shc A was expressed in Shc A transfected cells
Figure 16:
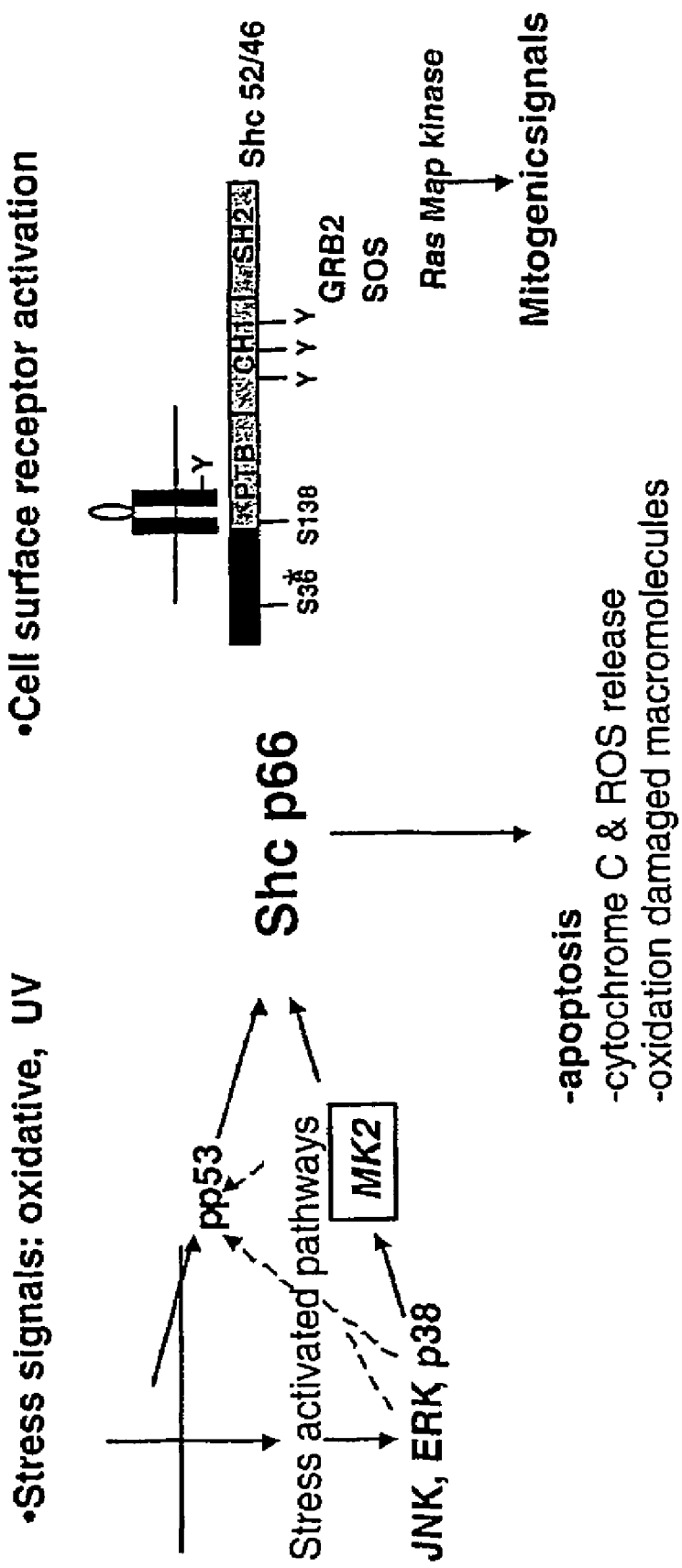
FIG. 16 is a schematic representation of stress activated pathways regulated by MK2 in response to cellular stress and phosphorylation of Shc in response to MK2 activation by cellular stress.

As depicted in FIG. 15B, MK2 phosphorylates p66 Shc A in vitro. MK2 may function in p66 Shc A regulated stress activated pathways. Although the 66 kDa isoform of Shc A does bind activated cell surface receptors, its binding does not lead to activation of the Ras MAPK pathway. Since p66 Shc A is not ubiquitously expressed, its cell type and tissue specific expression is proposed to selectively regulate activation of the Ras MAPK pathway through its selective expression pattern. Additionally, the p66 Shc A isoform acts downstream of p53 to regulate cellular responses to oxidative stress. (Trinei et al., Oncogene 21(24):3872-8 (2002)). The P38-MK2 pathway is activated by oxidative stress to phosphorylate small heat shock proteins thereby modulating microfilament responses to stress. (Huot et al., Circ Res. 80(3):383-92. 1997)). Both p38 and MK2 have been implicated in p53 phosphorylation upon oxidative stress. (She Q. B. et al., J Biol. Chem. 7;275(27):20444-9 (2000); She Q. B. et al., Oncogene 21(10):1580-9 (2002)). JNK and ERK have been implicated in serine phosphorylating p66. The data presented in this application supports a role for MK2 in stress activated phosphorylation of p66, as represented in FIG. 16.

Example 15

Phospho Akt and Phospho FKHR-L1 Levels were Reduced in MK2−/− Cells

Data generated from animals that are knock-outs for p66Shc A has shown that p66 regulates cellular responses to oxidative stress including generation of intracellular ROS and apoptosis and that phosphorylation at S36 in the protein is required for these responses. Cells derived from p66Shc A −/− animals have decreased levels of intracellular free radicals and are resistant to stress induced apoptosis compared with wild type littermates. In addition, p66Shc A −/− animals are resistant to paraquot, an oxidant-generating compound and further show an extended life span. Phosphorylation of both AKT and FKHR-L1 in response to oxidative stress such as UV light or $H_2O_2$, is reduced in p66Shc −/− MEFs. Reduction in FKHR-L1 phosphorylation correlates with an increase in FKHR-L1 activity, as this transcription factor remains nuclear in its de-phosphorylated form. Cells with activated FKHR-L1 are resistant to apoptosis consistent with the role of this transcription factor in regulating the expression of several antioxidant enzymes including superoxide dismutase and catalase.

Figure 17:
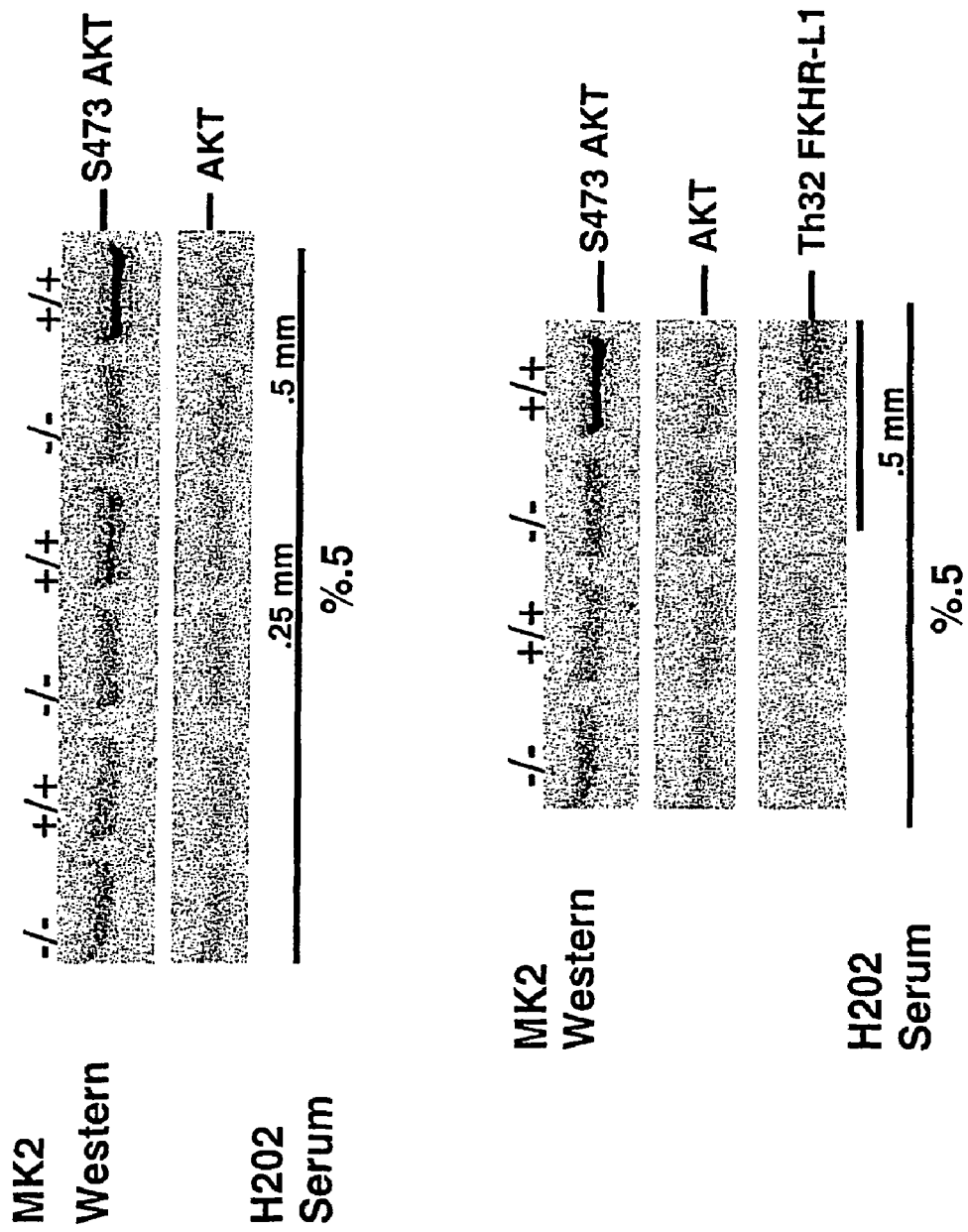
FIG. 17 depicts western blots to show levels of phosphorylated AKT and FKHR-L1 in response to hydrogen peroxide ($H_2O_2$) in MK2−/− and MK2+/+ mouse embryo fibroblasts (MEFs). As depicted, both phosphorylated AKT and phosphorylated FKHR-L1 levels were reduced in MK2−/− MEFs as compared to levels in MK2+/+ MEFs.

A role for MK2 in phosphorylating and regulating p66Shc A in cellular responses to stress suggests that cells deleted for MK2 should show reduced levels of both phospho (p)-AKT and phospho (p)-FKHR-L1 in response to oxidative stress as compared with wild type cells. In order to test this prediction, $H_2O_2$ induced p-AKT and p-FKHR-L1 levels in MK2−/− and +/+ MEFs were assayed. Quantitative western blot analysis showed that both p-AKT and p-FKHR-L1 levels were reduced in MK2−/− MEFs as compared with +/+ MEFs suggesting that intracellular ROS levels are reduced in MK2−/− cells (FIG. 17).

Example 16

Screening for Anti-Inflammatory Drugs

1. Yeast 2-Hybrid System for Drug-Screening

Proteins that bind MK2 are used for identifying anti-inflammatory drugs including small molecules, peptides, chemical agents and antibodies that are useful for treatment or prevention of inflammation.

MK2-interacting proteins are identified using the yeast 2-hybrid system described herein. MK2-interacting proteins are then assayed for their effect on MK2 activity by one or more of assays provided herein or those that are well known in the art. For example, an MK2 interacting protein will either increase MK2 activity, for example, as determined by MK2 kinase activity or TNF-α biosynthesis; inhibit MK2 activity; or have no effect on MK2 activity. MK2 interacting proteins that increase MK2 activity are desirable to use as candidates for screening for anti-inflammatory drugs.

A positive yeast clone showing an interaction between MK2 and an MK2 interacting protein which increases MK2 activity, as described above, is streaked on the appropriate selection plate as many times as the number of drug candidates or test compounds to be tested. As expected, each streaked colony will be positive for the interaction between MK2 and the interacting protein, as assayed by color and growth assays. Each colony is subsequently contacted with a different drug candidate to assay for an effect on the interaction between MK2 and the interacting protein. A drug candidate that inhibits the interaction between MK2 and the interacting protein, as assayed by a reduction in color and/or growth of the colonies on the appropriate media, will be a identified as a potential candidate for the treatment or prevention of inflammation.

The same assay can be used, for example, for identification of drug candidates for identification of drug candidates which promote an interaction between MK2 and an interacting protein, where the interacting protein inhibits MK2 activity. For example, a positive yeast clone showing an interaction between MK2 and an interaction protein which inhibits MK2 activity, at least partially, as assayed by one or more assays provided herein, can be streaked on the appropriate media. Each colony of the positive clone is subsequently contacted with a potential drug candidate or test compound. The drug candidates which lead to stronger growth as well as color in yeast specificity assays, described herein, are potential candidates for promoting an interaction between MK2 and an MK2 interacting protein, where the interacting protein inhibits MK2 activity.

2. In Vitro Reconstitution Assays for Drug-Screening

In vitro reconstitution assays can be used both for identification of anti-inflammatory drugs that block MK2 activity or block interaction between MK2 and an interacting protein, where the protein increases MK2 activity.

Additionally, an in vitro reconstitution system can also be used for formation of protein complexes including MK2 and at least one MK2 interacting protein, where such complexes can be subsequently used for identification of test compounds that modulate inflammation. The effect of a test compound on inflammation can be assayed either by determining whether the test compound inhibits or promotes complex formation or for its effect on MK2 activity. For example, an amount of a protein complex including MK2 and an interacting protein can be measured before and after contacting the protein complex with a test compound. A test compound which leads to a decrease in the amount of protein complex relative to the amount in absence of the test compound will be anti-inflammatory. Whereas, a test compound which leads to an increase in the amount of protein complex relative to the amount in the absence of the test compound will be pro-inflammatory.

For example, MK2 is synthesized using an in vitro transcription-translation system, such as the rabbit reticulocyte system supplied by Promega. The in vitro translated MK2 is first assayed for activity in one or more assays provided herein. Various drug candidates are subsequently added to the translated MK2 under the appropriate conditions and for appropriate periods of time, and MK2 activity is assayed again subsequent to the contact with a potential drug candidate. Those candidates which lead to inhibition or reduction in MK2 activity are identified as potential anti-inflammatory drugs. These drugs can be further validated for their effect on inflammation and on various pathways involved in inflammation in vivo in cells and in animal models for inflammation.

Similarly, an in vitro reconstituted system can also be used for identifying drugs which inhibit the interaction between MK2 and an interacting protein, where the interacting protein stimulates MK2 activity. For example, a composition including in vitro translated MK2 and an interacting protein, as identified by the Y2H system or co-immunoprecipitation assays, is treated with potential drug candidates. The candidates which inhibit the interaction between MK2 and the interacting protein, are identified as potential anti-inflammatory drugs. These drugs can subsequently be tested in vivo in cells and in animal models. In addition to in vitro translated proteins, purified proteins may also be used in in vitro reconstitution assays for identification of anti-inflammatory drugs.

Example 17

Treatment of Conditions Related to Inflammation

Compounds (such as proteins, peptides, antibodies, chemical agents, and small molecules) that interact with at least one of MK2 or an MK2 complex may be administered to patients suffering from a condition related to inflammation according to Table 1. Patients take the composition one time or at intervals, such as once daily, and the symptoms of their condition improve. For example, there will be a decrease in inflammation. This shows that the composition of the invention is predicted to be useful for the treatment of conditions related to inflammation.

TABLE 1

Administration of Compounds that Interact with MK2 or an MK2 Complex

| Patient | Condition | Route of Administration | Dosage | Dosage Frequency | Predicted Results |
|---|---|---|---|---|---|
| 1 | inflammatory bowel disease | subcutaneous | 25 mg | once daily | decrease in inflammation |
| 2 | inflammatory bowel disease | subcutaneous | 50 mg | once daily | decrease in inflammation |
| 3 | inflammatory bowel disease | subcutaneous | 50 mg | once weekly | decrease in inflammation |
| 4 | inflammatory bowel disease | subcutaneous | 50 mg | once monthly | decrease in inflammation |
| 5 | inflammatory bowel disease | rectal | 50 mg | once daily | decrease in inflammation |
| 6 | inflammatory bowel disease | rectal | 50 mg | once weekly | decrease in inflammation |
| 7 | inflammatory bowel disease | rectal | 50 mg | once monthly | decrease in inflammation |
| 8 | inflammatory bowel disease | intra-muscular | 25 mg | once daily | decrease in inflammation |
| 9 | inflammatory bowel disease | intra-muscular | 50 mg | once daily | decrease in inflammation |
| 10 | inflammatory bowel disease | intra-muscular | 50 mg | once weekly | decrease in inflammation |
| 11 | inflammatory bowel disease | intra-muscular | 50 mg | once monthly | decrease in inflammation |
| 12 | inflammatory bowel disease | intra-venous | 50 mg | once weekly | decrease in inflammation |
| 13 | Crohn's disease | subcutaneous | 50 mg | once daily | decrease in inflammation |
| 14 | Crohn's disease | subcutaneous | 50 mg | once weekly | decrease in inflammation |
| 15 | Crohn's disease | subcutaneous | 50 mg | once monthly | decrease in inflammation |
| 16 | Crohn's disease | rectal | 50 mg | once daily | decrease in inflammation |
| 17 | Crohn's disease | rectal | 50 mg | once weekly | decrease in inflammation |
| 18 | Crohn's disease | rectal | 50 mg | once monthly | decrease in inflammation |
| 19 | Crohn's disease | intra-muscular | 50 mg | once daily | decrease in inflammation |
| 20 | Crohn's disease | inter-venous | 50 mg | once weekly | decrease in inflammation |
| 21 | rheumatoid arthritis | subcutaneous | 50 mg | once daily | decrease in inflammation |
| 22 | rheumatoid arthritis | subcutaneous | 50 mg | once weekly | decrease in inflammation |
| 23 | rheumatoid arthritis | intra-muscular | 50 mg | once daily | decrease in inflammation |
| 24 | rheumatoid arthritis | intra-muscular | 50 mg | once weekly | decrease in inflammation |
| 25 | rheumatoid arthritis | intra-venous | 50 mg | once weekly | decrease in inflammation |

The specification is most thoroughly understood in light of the teachings of the references cited within the specification which are hereby incorporated by reference. The embodiments within the specification provide an illustration of embodiments of the invention and should not be construed to limit the scope of the invention. The skilled artisan readily recognizes that many other embodiments are encompassed by the invention. All publications, patent applications and patents cited and sequences identified by accession or database reference numbers in this disclosure are incorporated by reference in their entirety. To the extent the material incorporated by reference contradicts or is inconsistent with the present specification, the present specification will supercede any such material. The citation of any references herein is not an admission that such references are prior art to the present invention.

Many modifications and variations of this invention can be made without departing from its spirit and scope, as will be apparent to those skilled in the art. The specific embodiments described herein are offered by way of example only and are not meant to be limiting in any way. Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may very depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

---

We claim:

1. A screening assay to identify compounds that inhibit or promote formation of a protein complex, comprising
   (i) providing a two-hybrid assay system comprising:
   a) a first fusion protein comprising an MK2 polypeptide, wherein said MK2 polypeptide comprises a proline-rich region, a kinase catalytic domain, a threonine residue that can be phosphorylated by MAP kinase, and a nuclear localization signal; and
   b) a second fusion protein comprising a Shc polypeptide set forth as SEQ ID NO: 6, under conditions wherein the two proteins interact in the two hybrid assay system;
   (ii) measuring a level of interaction between the fusion proteins in the presence and in the absence of a test compound; and
   (iii) comparing the level of interaction of the fusion proteins,
   wherein a difference in the amount of complex in the presence of the test compound, relative to the amount of complex in the absence of the test compound indicates that the test compound inhibits or promotes complex formation.

2. The assay of claim 1, wherein an increase in the amount of complex in the presence of the test compound indicates that the test compound promotes complex formation.

3. The assay of claim 1, wherein a decrease in the amount of complex in the presence of the test compound indicates that the test compound inhibits complex formation.

4. The assay of claim 1, wherein the MK2 polypeptide comprises amino acids 1-370.

5. The assay of claim 1, wherein the MK2 polypeptide comprises amino acids 41-338.

6. The assay of claim 1, wherein the MK2 polypeptide has an arginine at position 93 in the ATP-binding pocket.

* * * * *

UNITED STATES PATENT AND TRADEMARK OFFICE
CERTIFICATE OF CORRECTION

PATENT NO. : 7,364,870 B2  Page 1 of 1
APPLICATION NO. : 10/523014
DATED : April 29, 2008
INVENTOR(S) : Yvonne M. Yannoni and Lih-Ling Lin It is certified that error appears in the above-identified patent and that said Letters Patent is hereby corrected as shown below:

In claim 1, Column 53, lines 40-43 delete ", wherein said MK2 polypeptide comprises a proline-rich region, a kinase catalytic domain, a threonine residue that can be phosphorylated by MAP kinase, and a nuclear localization signal;"

Signed and Sealed this

Eighth Day of July, 2008

JON W. DUDAS
*Director of the United States Patent and Trademark Office*

SEQUENCE LISTING

<160> NUMBER OF SEQ ID NOS: 6

<210> SEQ ID NO 1
<211> LENGTH: 3312
<212> TYPE: DNA
<213> ORGANISM: Homo sapiens

<400> SEQUENCE: 1

```
cccacgcgtc cggggacgg  ttgctgagcg ggcctgggac agcgggtcgc ggcacctccc    60
gcctgcgcgt gtctaatccg tctgtcgggt cccgaaagag ctaagccgag cctgcgccgg   120
acgggtgggc tggactgaga gaattctctg agctggtgac aggtgccaca ggcactgggg   180
atctcaccag aaaggaaccg acggagctag ggccagcga dgatggcggac gaggccttag   240
ctgggctgga tgagggagcc cttcggaagc tgctggaggt cacagcagat ctggcagagc   300
ggcggcgcat ccgctcagcc atccgggaac tgcagcggca ggagctggag cgcgaggagg   360
aggccctggc atccaagcgt ttccgtgccg agcggcagga caacaaggag aactggctgc   420
actctcagca gcgggaagct gagcagcggg ctgccctggc acggctggca gggcagctgg   480
agtccatgaa cgatgtggag gaattgactg cactgttgcg aagcgctggt gagtatgagg   540
agcgcaagct gatccgagct gccatccgcc gtgtacgggc tcaggagatt gaggctgcca   600
ccttggctgg gaggttgtac agcgggcgtc ccaacagtgg ctcaagagag gacagcaagg   660
ggctagcggc acacaggctg gaacagtgtg aggtgccaga gcgagaggaa caggaacagc   720
aggcagaggt ttcaaagcca acccccaccc ctgaaggcac cagccaggat gtgaccacag   780
tgacactcct gctgcgagcc ccacctggga gcacatccag ctcacctgcc tcacccagca   840
gttcacccac ccctgcctct cctgagcctc cattggagcc tgccgaggcc cagtgcctta   900
cagctgaggt tccaggcagc ccagagccac ccccagccc  acccaagacc accagccctg   960
agcctcagga gtctccaacg ctccccagca ctgagggcca ggtggtcaac aagcttctgt  1020
ctggccccaa agagacccct gctgcccaga gccccaccag aggcccctct gacaccaaga  1080
gagcagacgt ggctggaccc cgaccctgcc aacgctccct gtcggtgctc agcccccgcc  1140
aaccagccca gaaccgagag tccaccccccc ttgccagcgg accttcctca ttccagcggg  1200
ctggctctgt gcgggatcgt gtccacaagt tcacatctga ttctcctatg gctgctaggc  1260
tccaggatgg cacacccag gctgccctaa gtcccctgac ccccgcaagg ctcctgggcc  1320
cctccctcac cagcaccacc cctgcctcct cctcagcgg ctcctcctct cggggccca  1380
gtgatacctc ctcccggttc agcaaggagc aacgaggagt agcccagccc ctggcccagc  1440
ttcgaagctg cccccaggag gagggcccca ggggcgggg cttggctgct aggccccttg  1500
aaaacagagc aggggggcct gtggcacgtt cagaggagcc tggtgccccg ctgcccgtgg  1560
ccgtcggcac tgccgagcca gggggcagta tgaagaccac attcaccatc gagatcaagg  1620
acggccgtgg ccaggcctcc acaggccggg tgctgctgcc cacaggcaac cagagggcag  1680
aactgacact ggggctgcgg gcgccccga ccctactcag caccagtagt ggggcaaga  1740
gcaccatcac ccgtgtcaac agccctggga ccctggctcg gctgggcagt gtcactcatg  1800
tcaccagctt cagccatgcc ccccccagta gccgaggagg ctgcagcatc aagatggaac  1860
```

-continued

| | |
|---|---|
| cagagccagc agagcctctc gctgcagcag tggaagcggc caatggggct gagcagaccc | 1920 |
| gagtgaacaa agcaccagaa gggcggagcc ctctgagcgc tgaggagctg atgactattg | 1980 |
| aggatgaagg agtcttggac aagatgctgg atcagagcac ggactttgaa gagcggaagc | 2040 |
| tcatccgggc tgcacttcgt gagctccgac aaaggaagag agaccagcgg gacaaggagc | 2100 |
| gggaacggcg gctgcaggag gcacgggggcc ggccaggggga ggggcgcggc aacacagcca | 2160 |
| ctgagaccac cacgaggcac agccagcggg cagctgatgg ctctgctgtc agcactgtta | 2220 |
| ccaagactga gcggctcgtc cactccaatg atggcacacg gacggcccgc accaccacag | 2280 |
| tggagtcgag tttcgtgagg cgctcggaga atggcagtgg cagcaccatg atgcaaacca | 2340 |
| agaccttctc ctcttcctcc tcatccaaga agatgggcag catcttcgac cgcgaggacc | 2400 |
| aggccagccc acgggccggc agcctggcgg cgctcgagaa acggcaggcc gagaagaaga | 2460 |
| aagagctgat gaaggcgcag agtctgccca agacctcagc ctcccaggcg cgcaaggcca | 2520 |
| tgattgagaa gctggagaag gagggcgcgg ccggcagccc tggcggaccc cgcgcagccg | 2580 |
| tgcagcgatc caccagcttc ggggtcccca cgccaacag catcaagcag atgctgctgg | 2640 |
| actggtgtcg agccaagact cgcggctacg agcacgtcga catccagaac ttctcctcca | 2700 |
| gctggagtga tgggatggcc ttctgtgccc tggtgcacaa cttcttccct gaggccttcg | 2760 |
| actatgggca gcttagccct cagaaccgac gccagaactt cgaggtggcc ttctcatctg | 2820 |
| cggagaccca tgcggactgc ccgcagctcc tggatacaga ggacatggtg cggcttcgag | 2880 |
| agcctgactg gaagtgcgtg tacacgtaca tccaggaatt ctaccgctgt ctggtccaga | 2940 |
| aggggctggt aaaaaccaaa aagtcctaac ccctgctcgg ggccccacgg atgctggtgg | 3000 |
| actgtgtgcc cctggtggag gtggacgaca tgatgatcat gggcaagaag cctgacccca | 3060 |
| agtgtgtctt cacctatgtg cagtcgctct acaaccacct gcgacgccac gaactgcgcc | 3120 |
| tgcgcggcaa gaatgtctag cctgcccgcc cgcatggcca gccagtggca agctgccgcc | 3180 |
| cccactctcc gggcaccgtc tcctgcctgt gcgtccgccc accgctgccc tgtctgttgc | 3240 |
| gacaccctcc cccccacata cacacgcagc gttttgataa attattggtt ttcaacgaaa | 3300 |
| aaaaaaaaaa aa | 3312 |

<210> SEQ ID NO 2
<211> LENGTH: 2555
<212> TYPE: DNA
<213> ORGANISM: Homo sapiens

<400> SEQUENCE: 2

| | |
|---|---|
| ggcgccgcat gtgtctccgc ggcggctgca gccctcgagc gcccgccgcc gcgccccaac | 60 |
| cccgccgcc gccgccctc ccgccccggc ctcgcgcccc cgtccgggcc tcgcgccccg | 120 |
| gccgcccttt gttgacgccg gccaggccgt gcggtcggat gcgccgcggc agccccgggc | 180 |
| cccggctcga aggctcccgg ggcgagagga ggcggcccgc cggccgggac cccgcgcgag | 240 |
| tcggccccgg ccaggggctg cgtaggcccg cccggccagg cccagccgcc tggacagaga | 300 |
| cagggcaggg cattgttcat gcactgaccg acctcagcat ccccggcatg acctcaggga | 360 |
| acggaaactc tgcctccagc atcgccggca ctgccccca gaatggtgag aataaaccac | 420 |
| cacaggccat tgtgaaaccc caaatcctga cgcatgttat cgaagggttt gtgatccagg | 480 |
| aggggggcgga cgtttcccgg tgggacgctc gtctgctggt ggggaatctc aagaagaagt | 540 |
| atgcacaggg gttcctgcct gagaaacttc cacagcagga tcacaccacc accactgact | 600 |
| cggagatgga ggagccctat ctgcaagaat ccaaagagga gggtgctccc ctcaaactca | 660 |

```
agtgtgagct ctgtggccgg gtggactttg cctataagtt caagcgttcc aagcgcttct      720
gttccatggc ttgtgcaaag aggtacaacg tgggatgcac caaacgggtg ggacttttcc      780
actcagaccg gagcaagctg cagaaggcag gagctgcgac ccacaaccgc cgtcggccag      840
caaagccagt ctgccaccac ttaccaagga taccaagaag cagccaacag gcactgtgcc      900
cctttcggtt actgctgctt tgcgtaacac acagccagga agactccagc cgttgctcag      960
ataactcaag ctatgaggaa cccttgtcac ccatctcagc cagctcatct acttccgccg     1020
gcgacaaggc cagcgggacc tggagctccc cgacatgcat atgcgggacc tggtgggcat     1080
gggacaccac ttcctgccaa gtgagccacc aagtgaatgt agaagacgtc tacgaattca     1140
tccgctctct gccaggctgc caggagatag cagaggaatt ccgtgcccag gaaatcgacg     1200
ggcaagccct gctgctgctc aaggaggacc acctgatgag cgttatgaac atcaagctgg     1260
ggcccgccct gaagatctac gcccgcatca gcatgctcaa ggactcctag gctggtggc      1320 accaggattc tggcccaggg cgcctcctcc cgactgagca gagccagaca gacattcctg     1380
aggggcccag aaatggcggc gttggagggc aggggctctc cctagggca tagctggtga      1440 ggaggtctgg gcacctcctc catggctctc aggggccttt catttctgtg ggagggcag      1500 agaggtaggt ggcacagaag atggggcttt atgcttgtaa atattgatag cactggcttc     1560
ctccaaagtc ccaatactct agcccgctc tcttcccctc tttctgtccc ccattttcca      1620
gggggtatat ggtcagggct ccccaacctg agttggttac ttcaagggca gccagcaggc     1680
ctggatggag gcctagaaag cccttgcctt ccttcctccc acttctttct ccaggcctgg     1740
ttaactcttc cgttgtcagc ttctccccct tcagcctgtt tctgcagcag ccagggttct     1800
cccccctaca ccctctgcag gtggagagag agaagctggg cccagccgcg gtgcctgctg     1860
gccaagacgc cttaacgctg tgtgtatgac tgtgtgactg tgtgggagcc tggactgaca     1920
gataggccaa gggctactct ctggcatctc caggtgtttt gtagcaaaca gccacttagt     1980
gctttgtcct ggactccact cagcctcagg atggggaata ccaagaatg gcagcctcag      2040 cgcagaggca aggtcagaaa gagacggcgc ttcagagttt cctttccaga caccctccc      2100 cgcactgtga agttccctg accgcctcc tggttcacaa agagcattaa gaaagctgcg       2160
gtggtctgag caacatagcc cagacgtgga gcctcctggc ctgcctgccc gcccaccctg     2220
ggagtccagt ggtgaggctc agagaacttc taaggggaaa gaacagctgg agtttctgtt     2280
gatgtgaaga aggcagctct tggcctccca ctcccacact tctttgccta taaatcttcc     2340
tagcagcaat ttgagctacc tgaggaggag gcagggcaga agggcaaggg cctgcctctg     2400
acctgccgtg tcctttgcag gaaggaggta ggcacctttc tgagcttatt ctattccca      2460 cccacacccc caggcagggt tggaaatgaa ggacttttt  aacctttgtt ttgttttta      2520 aaaataaatc tgtaaaatct gaaaaaaaaa aaaaa                                2555

<210> SEQ ID NO 3
<211> LENGTH: 3664
<212> TYPE: DNA
<213> ORGANISM: Homo sapiens

<400> SEQUENCE: 3
atggggcctg aaactgtctg ggtctgagct ggggagcgga agccacttgt ccctctccct       60
ccccaggact tctgtgactc ctgggccaca gaggtccaac cagggtaagg gcctggggat      120
accccctgcc tggccccctt gcccaaactg gcagggggc caggctgggc agcagcccct       180
```

```
ctttcacctc aactatggat ctcctgcccc ccaagcccaa gtacaatcca ctccggaatg      240
agtctctgtc atcgctggag aaggggcttc tgggtccac cccccggag gagctgcctt       300 ccccatcagc ttcatccctg ggcccatcc tgcctcctct gcctggggac gatagtccca      360
ctaccctgtg ctccttcttc ccccggatga gcaacctgag gctggccaac ccggctgggg     420
ggcgcccagg gtctaagggg gagccaggaa gggcagctga tgatgggag gggatcgatg     480 gggcagccat gccagagtca ggcccctac ccctcctcca ggacatgaac aagctgagtg      540
gaggcggcgg gcgcaggact cgggtggaag ggggccagct tggggcgag gagtggaccc     600 gccacgggag ctttgtcaat aagcccacgc ggggctggct gcatcccaac gacaaagtca    660
tgggacccgg ggtttcctac ttggttcggt acatggggttg tgtggaggtc ctccagtcaa   720
tgcgtgccct ggacttcaac acccggactc aggtcaccag ggaggccatc agtctggtgt    780
gtgaggctgt gccgggtgct aaggggggcga caaggaggag aaagccctgt agccgcccgc   840
tcagctctat cctggggagg agtaacctga aatttgctgg aatgccaatc actctcaccg    900
tctccaccag cagcctcaac ctcatggccg cagactgcaa acagatcatc gccaaccacc    960
acatgcaatc tatctcattt gcatccggcg gggatccgga cacagccgag tatgtcgcct    1020
atgttgccaa agaccctgtg aatcagagag cctgccacat tctggagtgt cccgaagggc    1080
ttgcccagga tgtcatcagc accattggcc aggccttcga gttgcgcttc aaacaatacc    1140
tcaggaaccc acccaaactg gtcacccctc atgacaggat ggctggcttt gatggctcag    1200
catgggatga ggaggaggaa gagccacctg accatcagta ctataatgac ttcccgggga    1260
aggaaccccc cttggggggg gtggtagaca tgaggcttcg ggaaggagcc gctccagggg   1320
ctgctcgacc cactgcaccc aatgcccaga ccccagcca cttgggagct acattgcctg     1380
taggacagcc tgttggggga gatccagaag tccgcaaaca gatgccacct ccaccaccct    1440
gtccaggcag agagcttttt gatgatccct cctatgtcaa cgtccagaac ctagacaagg    1500
cccggcaagc agtgggtggt gctgggcccc caatcctgc tatcaatggc agtgcacccc    1560
gggacctgtt tgacatgaag cccttcgaag atgctcttcg ggtgcctcca cctccccagt    1620
cggtgtccat ggctgagcag ctccgagggg agccctggtt ccatgggaag ctgagccggc    1680
gggaggctga gcactgctg cagctcaatg gggacttctt ggtacgggag agcacgacca    1740
cacctggcca gtatgtgctc actggcttgc agagtgggca gcctaagcat ttgctactgg    1800
tggaccctga gggtgtggtt cggactaagg atcaccgctt tgaaagtgtc agtcacctta    1860
tcagctacca catggacaat cacttgccca tcatctctgc gggcagcgaa ctgtgtctac    1920
agcaacctgt ggagcggaaa ctgtgatctg ccctagcgct ctcttccaga agatgccctc    1980
caatcctttc caccctattc cctaactctc gggacctcgt tgggagtgt tctgtgggct    2040 tggccttgtg tcagagctgg gagtagcatg gactctgggt ttcatatcca gctgagtgag   2100
agggtttgag tcaaaagcct gggtgagaat cctgcctctc cccaaacatt aatcaccaaa    2160
gtattaatgt acagagtggc ccctcacctg ggcctttcct gtgccaacct gatgcccctt   2220
ccccaagaag gtgagtgctt gtcatggaaa atgtcctgtg gtgacaggcc cagtggaaca    2280
gtcacccttc tgggcaaggg ggaacaaatc acacctctgg gcttcagggt atcccagacc   2340
cctctcaaca cccgccccc ccatgtttaa actttgtgcc tttgaccatc tcttaggtct    2400
aatgatattt tatgcaaaca gttcttggac ccctgaattc ttcaatgaca gggatgccaa    2460
caccttcttg gcttctggga cctgtgttct tgctgagcac cctctccggt ttgggttggg    2520
ataacagagg caggagtggc agctgtcccc tctccctggg gatatgcaac ccttagagat    2580
```

-continued

```
tgccccagag ccccactccc ggccaggcgg gagatggacc cctcccttgc tcagtgcctc      2640
ctggccgggg cccctcaccc caagggggtct gtatatacat ttcataaggc ctgccctccc     2700
atgttgcatg cctatgtact ctgcgccaaa gtgcagccct tcctcctgaa gcctctgccc     2760
tgcctccctt tctgggaggg cggggtgggg gtgactgaat ttgggcctct tgtacagtta     2820
actctcccag gtggattttg tggaggtgag aaaaggggca ttgagactat aaagcagtag     2880
acaatcccca cataccatct gtagagttgg aactgcattc ttttaaagtt ttatatgcat     2940
atattttagg gctgctagac ttactttcct attttctttt ccattgctta ttcttgagca     3000
caaaatgata atcaattatt acatttatac atcaccttt tgacttttcc aagcccttt       3060 acagctcttg gcattttcct cgcctaggcc tgtgaggtaa ctgggatcgc acctttata     3120 ccagagacct gaggcagatg aaatttattt ccatctagga ctagaaaaac ttgggtctct     3180
taccgcgaga ctgagaggca gaagtcagcc cgaatgcctg tcagtttcat ggaggggaaa     3240
cgcaaaacct gcagttcctg agtaccttct acaggcccgg cccagcctag gcccggggtg     3300
gccacaccac agcaagccgg ccccccctct tttggccttg tggataaggg agagttgacc     3360
gttttcatcc tggcctcctt ttgctgtttg gatgtttcca cgggtctcac ttataccaaa     3420
gggaaaactc ttcattaaag tccgtatttc ttctaaaaaa aaaaaaaaaa aaatacattt     3480
atacatcacc tttttgactt ttccaagccc ttttacagct cttggcattt tcctcgccta     3540
ggcctgtgag gtaactggga tcgcacctt tataccagag acctgaggca gatgaaattt     3600
atttccatct aggactagaa aaacttgggt ctcttaccgc gagactgaga ggcagaagtc     3660
agcc                                                                  3664
```

<210> SEQ ID NO 4
<211> LENGTH: 915
<212> TYPE: PRT
<213> ORGANISM: Homo sapiens

<400> SEQUENCE: 4

```
Met Ala Asp Glu Ala Leu Ala Gly Leu Asp Glu Gly Ala Leu Arg Lys
1               5                   10                  15

Leu Leu Glu Val Thr Ala Asp Leu Ala Glu Arg Arg Ile Arg Ser
            20                  25                  30

Ala Ile Arg Glu Leu Gln Arg Gln Glu Leu Glu Arg Glu Glu Ala
        35                  40                  45

Leu Ala Ser Lys Arg Phe Arg Ala Glu Arg Gln Asp Asn Lys Glu Asn
    50                  55                  60

Trp Leu His Ser Gln Gln Arg Glu Ala Glu Gln Arg Ala Ala Leu Ala
65                  70                  75                  80

Arg Leu Ala Gly Gln Leu Glu Ser Met Asn Asp Val Glu Glu Leu Thr
                85                  90                  95

Ala Leu Leu Arg Ser Ala Gly Glu Tyr Glu Arg Lys Leu Ile Arg
            100                 105                 110

Ala Ala Ile Arg Arg Val Arg Ala Gln Glu Ile Glu Ala Ala Thr Leu
        115                 120                 125

Ala Gly Arg Leu Tyr Ser Gly Arg Pro Asn Ser Gly Ser Arg Glu Asp
    130                 135                 140

Ser Lys Gly Leu Ala Ala His Arg Leu Glu Gln Cys Glu Val Pro Glu
145                 150                 155                 160

Arg Glu Glu Gln Glu Gln Gln Ala Glu Val Ser Lys Pro Thr Pro Thr
                165                 170                 175
```

-continued

```
Pro Glu Gly Thr Ser Gln Asp Val Thr Thr Val Thr Leu Leu Leu Arg
            180                 185                 190

Ala Pro Pro Gly Ser Thr Ser Ser Pro Ala Ser Pro Ser Ser Ser
            195                 200                 205

Pro Thr Pro Ala Ser Pro Glu Pro Leu Glu Pro Ala Glu Ala Gln
            210                 215                 220

Cys Leu Thr Ala Glu Val Pro Gly Ser Pro Glu Pro Pro Ser Pro
225                 230                 235                 240

Pro Lys Thr Thr Ser Pro Glu Pro Gln Glu Ser Pro Thr Leu Pro Ser
                    245                 250                 255

Thr Glu Gly Gln Val Val Asn Lys Leu Leu Ser Gly Pro Lys Glu Thr
            260                 265                 270

Pro Ala Ala Gln Ser Pro Thr Arg Gly Pro Ser Asp Thr Lys Arg Ala
            275                 280                 285

Asp Val Ala Gly Pro Arg Pro Cys Gln Arg Ser Leu Ser Val Leu Ser
            290                 295                 300

Pro Arg Gln Pro Ala Gln Asn Arg Glu Ser Thr Pro Leu Ala Ser Gly
305                 310                 315                 320

Pro Ser Ser Phe Gln Arg Ala Gly Ser Val Arg Asp Arg Val His Lys
                    325                 330                 335

Phe Thr Ser Asp Ser Pro Met Ala Ala Arg Leu Gln Asp Gly Thr Pro
                    340                 345                 350

Gln Ala Ala Leu Ser Pro Leu Thr Pro Ala Arg Leu Leu Gly Pro Ser
                    355                 360                 365

Leu Thr Ser Thr Thr Pro Ala Ser Ser Ser Gly Ser Ser Ser Arg
            370                 375                 380

Gly Pro Ser Asp Thr Ser Ser Arg Phe Ser Lys Glu Gln Arg Gly Val
385                 390                 395                 400

Ala Gln Pro Leu Ala Gln Leu Arg Ser Cys Pro Gln Glu Glu Gly Pro
                    405                 410                 415

Arg Gly Arg Gly Leu Ala Ala Arg Pro Leu Glu Asn Arg Ala Gly Gly
                    420                 425                 430

Pro Val Ala Arg Ser Glu Glu Pro Gly Ala Pro Leu Pro Val Ala Val
            435                 440                 445

Gly Thr Ala Glu Pro Gly Gly Ser Met Lys Thr Thr Phe Thr Ile Glu
            450                 455                 460

Ile Lys Asp Gly Arg Gly Gln Ala Ser Thr Gly Arg Val Leu Leu Pro
465                 470                 475                 480

Thr Gly Asn Gln Arg Ala Glu Leu Thr Leu Gly Leu Arg Ala Pro Pro
                    485                 490                 495

Thr Leu Leu Ser Thr Ser Ser Gly Gly Lys Ser Thr Ile Thr Arg Val
            500                 505                 510

Asn Ser Pro Gly Thr Leu Ala Arg Leu Gly Ser Val Thr His Val Thr
            515                 520                 525

Ser Phe Ser His Ala Pro Pro Ser Ser Arg Gly Gly Cys Ser Ile Lys
            530                 535                 540

Met Glu Pro Glu Pro Ala Glu Pro Leu Ala Ala Ala Val Glu Ala Ala
545                 550                 555                 560

Asn Gly Ala Glu Gln Thr Arg Val Asn Lys Ala Pro Glu Gly Arg Ser
                    565                 570                 575

Pro Leu Ser Ala Glu Glu Leu Met Thr Ile Glu Asp Glu Gly Val Leu
            580                 585                 590
```

```
Asp Lys Met Leu Asp Gln Ser Thr Asp Phe Glu Glu Arg Lys Leu Ile
        595                 600                 605

Arg Ala Ala Leu Arg Glu Leu Arg Gln Arg Lys Arg Asp Gln Arg Asp
    610                 615                 620

Lys Glu Arg Glu Arg Arg Leu Gln Glu Ala Arg Gly Arg Pro Gly Glu
625                 630                 635                 640

Gly Arg Gly Asn Thr Ala Thr Glu Thr Thr Arg His Ser Gln Arg
            645                 650                 655

Ala Ala Asp Gly Ser Ala Val Ser Thr Val Thr Lys Thr Glu Arg Leu
                660                 665                 670

Val His Ser Asn Asp Gly Thr Thr Ala Arg Thr Thr Thr Val Glu
            675                 680                 685

Ser Ser Phe Val Arg Arg Ser Glu Asn Gly Ser Gly Ser Thr Met Met
        690                 695                 700

Gln Thr Lys Thr Phe Ser Ser Ser Ser Ser Lys Lys Met Gly Ser
705                 710                 715                 720

Ile Phe Asp Arg Glu Asp Gln Ala Ser Pro Arg Ala Gly Ser Leu Ala
                725                 730                 735

Ala Leu Glu Lys Arg Gln Ala Glu Lys Lys Glu Leu Met Lys Ala
        740                 745                 750

Gln Ser Leu Pro Lys Thr Ser Ala Ser Gln Ala Arg Lys Ala Met Ile
    755                 760                 765

Glu Lys Leu Glu Lys Glu Gly Ala Ala Gly Ser Pro Gly Gly Pro Arg
770                 775                 780

Ala Ala Val Gln Arg Ser Thr Ser Phe Gly Val Pro Asn Ala Asn Ser
785                 790                 795                 800

Ile Lys Gln Met Leu Leu Asp Trp Cys Arg Ala Lys Thr Arg Gly Tyr
                805                 810                 815

Glu His Val Asp Ile Gln Asn Phe Ser Ser Ser Trp Ser Asp Gly Met
        820                 825                 830

Ala Phe Cys Ala Leu Val His Asn Phe Phe Pro Glu Ala Phe Asp Tyr
    835                 840                 845

Gly Gln Leu Ser Pro Gln Asn Arg Arg Gln Asn Phe Glu Val Ala Phe
850                 855                 860

Ser Ser Ala Glu Thr His Ala Asp Cys Pro Gln Leu Leu Asp Thr Glu
865                 870                 875                 880

Asp Met Val Arg Leu Arg Glu Pro Asp Trp Lys Cys Val Tyr Thr Tyr
                885                 890                 895

Ile Gln Glu Phe Tyr Arg Cys Leu Val Gln Lys Gly Leu Val Lys Thr
        900                 905                 910

Lys Lys Ser
        915

<210> SEQ ID NO 5
<211> LENGTH: 433
<212> TYPE: PRT
<213> ORGANISM: Homo sapiens

<400> SEQUENCE: 5

Met Cys Leu Arg Gly Gly Cys Ser Pro Arg Ala Pro Ala Ala Ala Pro
1               5                   10                  15

Gln Pro Arg Pro Pro Ala Leu Pro Arg Pro Arg Ala Pro Val
            20                  25                  30

Pro Ala Ser Arg Pro Gly Arg Pro Leu Leu Thr Pro Ala Arg Pro Cys
        35                  40                  45
```

Gly Arg Met Arg Arg Gly Ser Pro Gly Pro Arg Leu Gly Gly Ser Arg
    50                  55                  60

Gly Glu Arg Arg Pro Ala Gly Arg Asp Pro Ala Arg Val Gly Pro
65                  70                  75                  80

Gly Gln Gly Leu Arg Arg Pro Ala Arg Pro Gly Pro Ala Ala Trp Thr
                85                  90                  95

Glu Thr Gly Gln Gly Ile Val His Ala Leu Thr Asp Leu Ser Ile Pro
                100                 105                 110

Gly Met Thr Ser Gly Asn Gly Asn Ser Ala Ser Ser Ile Ala Gly Thr
                115                 120                 125

Ala Pro Gln Asn Gly Glu Asn Lys Pro Gln Ala Ile Val Lys Pro
    130                 135                 140

Gln Ile Leu Thr His Val Ile Glu Gly Phe Val Ile Gln Glu Gly Ala
145                 150                 155                 160

Asp Val Ser Arg Trp Asp Ala Arg Leu Leu Val Gly Asn Leu Lys Lys
                165                 170                 175

Lys Tyr Ala Gln Gly Phe Leu Pro Glu Lys Leu Pro Gln Gln Asp His
                180                 185                 190

Thr Thr Thr Thr Asp Ser Glu Met Glu Glu Pro Tyr Leu Gln Glu Ser
                195                 200                 205

Lys Glu Glu Gly Ala Pro Leu Lys Leu Lys Cys Glu Leu Cys Gly Arg
    210                 215                 220

Val Asp Phe Ala Tyr Lys Phe Lys Arg Ser Lys Arg Phe Cys Ser Met
225                 230                 235                 240

Ala Cys Ala Lys Arg Tyr Asn Val Gly Cys Thr Lys Arg Val Gly Leu
                245                 250                 255

Phe His Ser Asp Arg Ser Lys Leu Gln Lys Ala Gly Ala Ala Thr His
                260                 265                 270

Asn Arg Arg Arg Pro Ala Lys Pro Val Cys His His Leu Pro Arg Ile
    275                 280                 285

Pro Arg Ser Ser Gln Gln Ala Leu Cys Pro Phe Arg Leu Leu Leu Leu
    290                 295                 300

Cys Val Thr His Ser Gln Glu Asp Ser Ser Arg Cys Ser Asp Asn Ser
305                 310                 315                 320

Ser Tyr Glu Glu Pro Leu Ser Pro Ile Ser Ala Ser Ser Thr Ser
                325                 330                 335

Ala Gly Asp Lys Ala Ser Gly Thr Trp Ser Ser Pro Thr Cys Ile Cys
                340                 345                 350

Gly Thr Trp Trp Ala Trp Asp Thr Thr Ser Cys Gln Val Ser His Gln
                355                 360                 365

Val Asn Val Glu Asp Val Tyr Glu Phe Ile Arg Ser Leu Pro Gly Cys
    370                 375                 380

Gln Glu Ile Ala Glu Glu Phe Arg Ala Gln Glu Ile Asp Gly Gln Ala
385                 390                 395                 400

Leu Leu Leu Leu Lys Glu Asp His Leu Met Ser Val Met Asn Ile Lys
                405                 410                 415

Leu Gly Pro Ala Leu Lys Ile Tyr Ala Arg Ile Ser Met Leu Lys Asp
                420                 425                 430

Ser

<210> SEQ ID NO 6
<211> LENGTH: 578
<212> TYPE: PRT

<213> ORGANISM: Homo sapiens

<400> SEQUENCE: 6

```
Met Asp Leu Leu Pro Pro Lys Pro Lys Tyr Asn Pro Leu Arg Asn Glu
1               5                   10                  15

Ser Leu Ser Ser Leu Glu Glu Gly Ala Ser Gly Ser Thr Pro Pro Glu
            20                  25                  30

Glu Leu Pro Ser Pro Ser Ala Ser Ser Leu Gly Pro Ile Leu Pro Pro
        35                  40                  45

Leu Pro Gly Asp Asp Ser Pro Leu Pro Cys Val Pro Ser Phe Pro Arg
    50                  55                  60

Met Ser Asn Leu Lys Leu Ala Asn Pro Ala Gly Gly Pro Trp Gly Leu
65                  70                  75                  80

Lys Gly Ser Gln Glu Arg Leu Lys Met Gly Lys Gly Val Gln Gln Gly
                85                  90                  95

Gln Pro Phe Gly Leu Arg Pro Leu Ala Pro Pro Asp Met Asn Lys Leu
            100                 105                 110

Ser Gly Gly Gly Gly Arg Arg Thr Arg Val Glu Gly Gly Gln Leu Gly
        115                 120                 125

Gly Glu Glu Trp Thr Arg His Gly Ser Phe Val Asn Lys Pro Thr Arg
130                 135                 140

Gly Trp Leu His Pro Asn Asp Lys Val Met Gly Pro Gly Val Ser Tyr
                150                 155                 160

Leu Val Arg Tyr Met Gly Cys Val Glu Val Leu Gln Ser Met Arg Ala
            165                 170                 175

Leu Asp Phe Asn Thr Arg Thr Gln Val Thr Arg Glu Ala Ile Ser Leu
        180                 185                 190

Val Cys Glu Ala Val Pro Gly Ala Lys Gly Ala Thr Arg Arg Arg Lys
    195                 200                 205

Pro Cys Ser Arg Pro Leu Ser Ser Ile Leu Gly Arg Ser Asn Leu Lys
210                 215                 220

Phe Ala Gly Met Pro Ile Thr Leu Thr Val Ser Thr Ser Ser Leu Asn
225                 230                 235                 240

Leu Met Ala Ala Asp Cys Lys Gln Ile Ile Ala Asn His His Met Gln
            245                 250                 255

Ser Ile Ser Phe Ala Ser Gly Gly Asp Pro Asp Thr Ala Glu Tyr Val
        260                 265                 270

Ala Tyr Val Ala Lys Asp Pro Val Asn Gln Arg Ala Cys His Ile Leu
    275                 280                 285

Glu Cys Pro Glu Gly Leu Ala Gln Asp Val Ile Ser Thr Ile Gly Gln
290                 295                 300

Ala Phe Glu Leu Arg Phe Lys Gln Tyr Leu Arg Asn Pro Pro Lys Leu
305                 310                 315                 320

Val Thr Pro His Asp Arg Met Ala Gly Phe Asp Gly Ser Ala Trp Asp
            325                 330                 335

Glu Glu Glu Glu Pro Pro Asp His Gln Tyr Tyr Asn Asp Phe Pro
        340                 345                 350

Gly Lys Glu Pro Pro Leu Gly Gly Val Val Asp Met Arg Leu Arg
    355                 360                 365

Glu Gly Ala Ala Arg Pro Thr Leu Pro Ser Ala Gln Met Ser Ser His
370                 375                 380

Leu Gly Ala Thr Leu Pro Ile Gly Gln His Ala Ala Gly Asp His Glu
385                 390                 395                 400
```

-continued

```
Val Arg Lys Gln Met Leu Pro Pro Pro Cys Pro Gly Arg Glu Leu
                405             410             415

Phe Asp Asp Pro Ser Tyr Val Asn Ile Gln Asn Leu Asp Lys Ala Arg
            420             425             430

Gln Ala Gly Gly Gly Ala Gly Pro Pro Asn Pro Ser Leu Asn Gly Ser
        435             440             445

Ala Pro Arg Asp Leu Phe Asp Met Lys Pro Phe Glu Asp Ala Leu Arg
    450             455             460

Val Pro Pro Pro Pro Gln Ser Met Ser Met Ala Glu Gln Leu Gln Gly
465             470             475             480

Glu Pro Trp Phe His Gly Lys Leu Ser Arg Arg Glu Ala Glu Ala Leu
            485             490             495

Leu Gln Leu Asn Gly Asp Phe Leu Val Arg Glu Ser Thr Thr Thr Pro
            500             505             510

Gly Gln Tyr Val Leu Thr Gly Leu Gln Ser Gly Gln Pro Lys His Leu
        515             520             525

Leu Leu Val Asp Pro Glu Gly Val Val Arg Thr Lys Asp His Arg Phe
    530             535             540

Glu Ser Val Ser His Leu Ile Ser Tyr His Met Asp Asn His Leu Pro
545             550             555             560

Ile Ile Ser Ala Gly Ser Glu Leu Cys Leu Gln Gln Pro Val Asp Arg
            565             570             575

Lys Val
```